United States Patent
Zamore

(10) Patent No.: US 7,749,585 B2
(45) Date of Patent: Jul. 6, 2010

(54) REDUCED PROFILE MEDICAL BALLOON ELEMENT

(76) Inventor: Alan Zamore, 600 Chestnut Ridge Rd., Chestnut Ridge, NY (US) 10977

( * ) Notice: Subject to any disclaimer, the term of this patent is extended or adjusted under 35 U.S.C. 154(b) by 1758 days.

(21) Appl. No.: 10/688,292

(22) Filed: Oct. 17, 2003

(65) Prior Publication Data
US 2004/0093008 A1  May 13, 2004

Related U.S. Application Data

(63) Continuation-in-part of application No. 09/558,355, filed on Apr. 26, 2000, now Pat. No. 6,656,550, which is a continuation-in-part of application No. 08/947,000, filed on Oct. 8, 1997, now Pat. No. 6,596,818, which is a continuation-in-part of application No. 08/727,145, filed on Oct. 8, 1996, now Pat. No. 5,900,444.

(60) Provisional application No. 60/420,735, filed on Oct. 24, 2002.

(51) Int. Cl.
B29D 23/00 (2006.01)
(52) U.S. Cl. .................. 428/35.1; 428/34.9; 428/36.92; 604/192; 604/194
(58) Field of Classification Search .................. None
See application file for complete search history.

(56) References Cited

U.S. PATENT DOCUMENTS

| | | | |
|---|---|---|---|
| 3,616,364 A | 10/1971 | D'Alelio | |
| 3,642,964 A | 2/1972 | Rausch, Jr. et al. | |
| 3,658,670 A | 4/1972 | Holicky et al. | |
| 3,674,743 A | 7/1972 | Verdol et al. | |
| 3,719,539 A | 3/1973 | Lamb et al. | |
| 3,871,908 A | 3/1975 | Spoor et al. | |
| 3,911,202 A | 10/1975 | Stine et al. | |
| 4,013,806 A | 3/1977 | Volkert et al. | |
| 4,025,407 A | 5/1977 | Chang et al. | |
| 4,065,589 A | 12/1977 | Lenard et al. | |

(Continued)

FOREIGN PATENT DOCUMENTS

CA  901410  5/1972

(Continued)

OTHER PUBLICATIONS

"Radiation Crosslinked Thermoplastic Polyurethane," International Polymer Science and Technology, vol. 19, No. 1, pp. T/6-T/9 (1992).

Primary Examiner—Monique R Jackson

(57) ABSTRACT

Medical dilatation balloons comprise a polymer that has the attribute of memory, and/or is crosslinked to impart memory. Such balloons exhibit a reduced tendency to overinflate at high inflation pressures. Furthermore, such balloons when shrunk radially by the application of heat while restraining axial shrinkage, exhibit customizable linear or non-linear compliance curves and lower crosslinking profile relative to the same balloon when unshrunk. Also disclosed is an expansive element within a tube whose outer diameter is equal to the outer diameter of the tube from which it was made. In addition, disclosed are (a) processes for preparing crosslinkable polymers, (b) joining crosslinked balloons to catheter systems, (c) forming shrunk balloon elements, and (d) forming an expansive element within a tube whose outer diameter is equal to the outer diameter of the tube from which it was made.

25 Claims, 8 Drawing Sheets

U.S. PATENT DOCUMENTS

| | | | |
|---|---|---|---|
| 4,101,699 A | 7/1978 | Stine et al. | |
| 4,133,731 A | 1/1979 | Hansen et al. | |
| 4,151,057 A | 4/1979 | St. Clair et al. | |
| 4,154,244 A | 5/1979 | Becker et al. | |
| 4,254,774 A | 3/1981 | Boretos | |
| 4,255,552 A | 3/1981 | Schollenberger et al. | |
| 4,264,658 A | 4/1981 | Tobias et al. | |
| 4,266,005 A | 5/1981 | Nakamura et al. | |
| 4,275,180 A * | 6/1981 | Clarke | 525/173 |
| 4,289,682 A | 9/1981 | Peters | |
| 4,323,071 A | 4/1982 | Simpson et al. | |
| 4,331,697 A | 5/1982 | Kudo et al. | |
| 4,331,786 A | 5/1982 | Foy et al. | |
| 4,332,920 A | 6/1982 | Foy et al. | |
| 4,342,793 A | 8/1982 | Skinner et al. | |
| 4,358,354 A | 11/1982 | Iida et al. | |
| 4,385,635 A | 5/1983 | Ruiz | |
| 4,413,989 A | 11/1983 | Schejeldahl et al. | |
| 4,443,588 A | 4/1984 | Fukuda et al. | |
| 4,444,816 A | 4/1984 | Richards et al. | |
| 4,467,002 A * | 8/1984 | Crofts | 428/34.9 |
| 4,490,421 A | 12/1984 | Levy | |
| 4,552,815 A | 11/1985 | Dreher et al. | |
| 4,563,181 A | 1/1986 | Wijayarathna et al. | |
| 4,567,083 A | 1/1986 | Arioka et al. | |
| 4,580,568 A | 4/1986 | Gianturco | |
| 4,607,084 A | 8/1986 | Morris | |
| 4,608,984 A | 9/1986 | Fogarty | |
| 4,649,922 A | 3/1987 | Wiktor | |
| 4,654,233 A | 3/1987 | Grant et al. | |
| 4,655,771 A | 4/1987 | Wallsten | |
| 4,675,361 A | 6/1987 | Ward, Jr. | |
| 4,681,110 A | 7/1987 | Wiktor | |
| 4,687,689 A | 8/1987 | Yazaki et al. | |
| 4,705,517 A | 11/1987 | DiPisa, Jr. | |
| 4,733,665 A | 3/1988 | Palmaz | |
| 4,740,207 A | 4/1988 | Kreamer | |
| 4,760,849 A | 8/1988 | Kropf | |
| 4,762,884 A | 8/1988 | Goyert et al. | |
| 4,776,337 A | 10/1988 | Palmaz | |
| 4,786,556 A | 11/1988 | Hu et al. | |
| 4,795,458 A | 1/1989 | Regan | |
| 4,800,882 A | 1/1989 | Gianturco | |
| 4,820,270 A | 4/1989 | Hardcastle et al. | |
| 4,820,782 A | 4/1989 | Ueno | |
| 4,822,361 A * | 4/1989 | Okita et al. | 623/23.71 |
| 4,830,003 A | 5/1989 | Wolff et al. | |
| RE32,983 E | 7/1989 | Levy | |
| 4,856,516 A | 8/1989 | Hillstead | |
| 4,871,811 A | 10/1989 | Gaku et al. | |
| 4,877,030 A | 10/1989 | Beck et al. | |
| 4,884,573 A | 12/1989 | Wijay et al. | |
| 4,886,062 A | 12/1989 | Wiktor | |
| 4,886,506 A | 12/1989 | Lovegren | |
| 4,897,433 A | 1/1990 | Sugo et al. | |
| 4,898,591 A | 2/1990 | Jang et al. | |
| 4,906,244 A | 3/1990 | Pinchuk et al. | |
| 4,907,336 A | 3/1990 | Gianturco | |
| 4,913,141 A | 4/1990 | Hillstead | |
| 4,917,667 A | 4/1990 | Jackson | |
| 4,922,905 A | 5/1990 | Strecker | |
| 4,923,464 A | 5/1990 | DiPisa, Jr. | |
| 4,938,676 A | 7/1990 | Jackowski et al. | |
| 4,948,859 A | 8/1990 | Echols et al. | |
| 4,950,239 A | 8/1990 | Gahara et al. | |
| 4,950,257 A | 8/1990 | Hibbs et al. | |
| 4,952,357 A | 8/1990 | Euteneuer | |
| 4,954,126 A | 9/1990 | Wallsten | |
| 4,964,853 A | 10/1990 | Sugiyama et al. | |
| 4,969,890 A | 11/1990 | Sugita et al. | |
| 4,990,151 A | 2/1991 | Wallsten | |
| 4,990,155 A | 2/1991 | Wilkoff | |
| 4,994,032 A | 2/1991 | Sugiyama et al. | |
| 4,994,071 A | 2/1991 | MacGregor | |
| RE33,561 E | 3/1991 | Levy | |
| 5,007,926 A | 4/1991 | Derbyshire | |
| 5,019,090 A | 5/1991 | Pinchuk | |
| 5,035,706 A | 7/1991 | Gianturco et al. | |
| 5,041,126 A | 8/1991 | Gianturco | |
| 5,059,211 A | 10/1991 | Stack et al. | |
| 5,061,275 A | 10/1991 | Wallsten et al. | |
| 5,064,435 A | 11/1991 | Porter | |
| 5,078,726 A | 1/1992 | Kreamer | |
| 5,084,529 A | 1/1992 | Crano | |
| 5,089,006 A | 2/1992 | Stiles | |
| 5,092,841 A | 3/1992 | Spears | |
| 5,092,877 A | 3/1992 | Pinchuk | |
| 5,104,399 A | 4/1992 | Lazarus | |
| 5,104,404 A | 4/1992 | Wolff | |
| 5,108,415 A | 4/1992 | Pinchuk et al. | |
| 5,108,416 A | 4/1992 | Ryan et al. | |
| 5,108,417 A | 4/1992 | Sawyer | |
| 5,109,097 A | 4/1992 | Klun et al. | |
| 5,116,309 A | 5/1992 | Coll | |
| 5,116,318 A | 5/1992 | Hillstead | |
| 5,116,360 A | 5/1992 | Pinchuk et al. | |
| 5,116,652 A | 5/1992 | Alzner | |
| 5,122,154 A | 6/1992 | Rhodes | |
| 5,123,917 A | 6/1992 | Lee | |
| 5,133,732 A | 7/1992 | Wiktor | |
| 5,135,536 A | 8/1992 | Hillstead | |
| 5,147,385 A | 9/1992 | Beck et al. | |
| 5,156,612 A | 10/1992 | Pinchuk et al. | |
| 5,163,952 A | 11/1992 | Froix | |
| 5,171,262 A | 12/1992 | MacGregor | |
| 5,192,297 A | 3/1993 | Hull | |
| 5,195,984 A | 3/1993 | Schatz | |
| 5,226,880 A | 7/1993 | Martin | |
| 5,234,457 A | 8/1993 | Andersen | |
| 5,236,659 A | 8/1993 | Pinchuk et al. | |
| 5,236,978 A | 8/1993 | Selvig et al. | |
| 5,246,420 A | 9/1993 | Kraus et al. | |
| 5,250,069 A | 10/1993 | Nobuyoshi et al. | |
| 5,264,260 A | 11/1993 | Saab | |
| 5,266,669 A | 11/1993 | Onwunaka et al. | |
| 5,281,677 A | 1/1994 | Onwunaka et al. | |
| 5,282,824 A | 2/1994 | Gianturco | |
| 5,284,883 A | 2/1994 | Ueno et al. | |
| 5,290,306 A | 3/1994 | Trotta et al. | |
| 5,292,331 A | 3/1994 | Boneau | |
| 5,295,978 A | 3/1994 | Fan et al. | |
| 5,300,048 A | 4/1994 | Drewes, Jr. et al. | |
| 5,304,134 A | 4/1994 | Kraus et al. | |
| 5,304,135 A | 4/1994 | Shonk | |
| 5,304,197 A | 4/1994 | Pinchuk et al. | |
| 5,304,340 A | 4/1994 | Downey | |
| 5,328,468 A | 7/1994 | Kaneko et al. | |
| 5,328,940 A | 7/1994 | Zimmer | |
| 5,334,148 A | 8/1994 | Martin | |
| 5,334,201 A | 8/1994 | Cowan | |
| 5,335,675 A | 8/1994 | Wheeler et al. | |
| 5,336,585 A | 8/1994 | Takahashi et al. | |
| 5,342,386 A | 8/1994 | Trotta | |
| 5,344,400 A | 9/1994 | Kaneko et al. | |
| 5,348,538 A | 9/1994 | Wang et al. | |
| 5,358,486 A | 10/1994 | Saab | |
| 5,374,704 A | 12/1994 | Müller et al. | |
| 5,382,633 A | 1/1995 | Scott et al. | |
| 5,397,306 A | 3/1995 | Nobuyoshi et al. | |
| 5,403,340 A | 4/1995 | Wang et al. | |
| 5,433,713 A | 7/1995 | Trotta | |
| 5,438,106 A | 8/1995 | Siranovich et al. | |
| 5,442,036 A | 8/1995 | Beavers et al. | |
| 5,455,308 A | 10/1995 | Bastiaansen | |

| | | |
|---|---|---|
| 5,490,838 A | 2/1996 | Miller |
| 5,500,180 A | 3/1996 | Anderson et al. |
| 5,500,181 A | 3/1996 | Wang et al. |
| 5,511,965 A | 4/1996 | Batdorf et al. |
| 5,545,133 A | 8/1996 | Burns et al. |
| 5,554,120 A | 9/1996 | Chen et al. |
| 5,556,383 A | 9/1996 | Wang et al. |
| 5,565,523 A | 10/1996 | Chen et al. |
| 5,576,072 A | 11/1996 | Hostettler et al. |
| 5,603,722 A | 2/1997 | Phan et al. |
| 5,733,496 A | 3/1998 | Avellanet |
| 5,747,591 A | 5/1998 | Chen et al. |
| 5,755,707 A | 5/1998 | Miyagawa et al. |
| 5,779,729 A | 7/1998 | Severini |
| 5,786,426 A | 7/1998 | Sperling et al. |
| 5,830,182 A | 11/1998 | Wang et al. |
| 5,849,846 A | 12/1998 | Chen et al. |
| 5,879,369 A | 3/1999 | Ishida |
| 5,900,444 A | 5/1999 | Zamore |
| 5,921,957 A | 7/1999 | Killion et al. |
| 5,951,941 A | 9/1999 | Wang et al. |
| 5,954,744 A | 9/1999 | Phan et al. |
| 5,993,415 A | 11/1999 | O'Neil et al. |
| 5,998,551 A | 12/1999 | O'Neil et al. |
| 6,022,341 A | 2/2000 | Lentz |
| 6,090,099 A | 7/2000 | Samson et al. |
| 6,110,142 A | 8/2000 | Pinchuk et al. |
| 6,123,718 A | 9/2000 | Tu et al. |
| 6,200,290 B1 | 3/2001 | Burgmeier |
| 6,238,408 B1 | 5/2001 | Kawabata et al. |
| 6,245,103 B1 | 6/2001 | Stinson |
| 6,290,485 B1 | 9/2001 | Wang |
| 6,402,778 B2 | 6/2002 | Wang |
| 6,429,232 B1 | 8/2002 | Kinsella et al. |
| 6,946,174 B1 * | 9/2005 | Chen .................... 428/35.7 |
| 7,108,826 B2 * | 9/2006 | Wang et al. ............ 264/573 |
| 7,465,483 B2 * | 12/2008 | Colone .................. 428/36.9 |
| 2002/0087165 A1 | 7/2002 | Lee et al. |

FOREIGN PATENT DOCUMENTS

| | | |
|---|---|---|
| EP | 117093 | 8/1984 |
| EP | 0-214-602 | 3/1987 |
| EP | 274411 | 7/1988 |
| EP | 513459 | 11/1992 |
| EP | 537069 | 4/1993 |
| EP | 540858 | 5/1993 |
| EP | 420488 | 7/1993 |
| EP | 566755 | 10/1993 |
| EP | 592885 | 4/1994 |
| EP | 697219 | 2/1996 |
| FR | 2651681 | 2/1983 |
| JP | 58-188463 | 11/1983 |
| JP | 61174256 | 8/1986 |
| WO | WO-82/02048 | 6/1982 |
| WO | WO-8401513 | 4/1984 |
| WO | WO-9001345 | 2/1990 |
| WO | WO-9208512 | 5/1992 |
| WO | WO-9219316 | 11/1992 |
| WO | WO-9523619 | 9/1995 |
| WO | WO-98/55171 | 12/1998 |
| WO | WO01/19425 | 3/2001 |

* cited by examiner

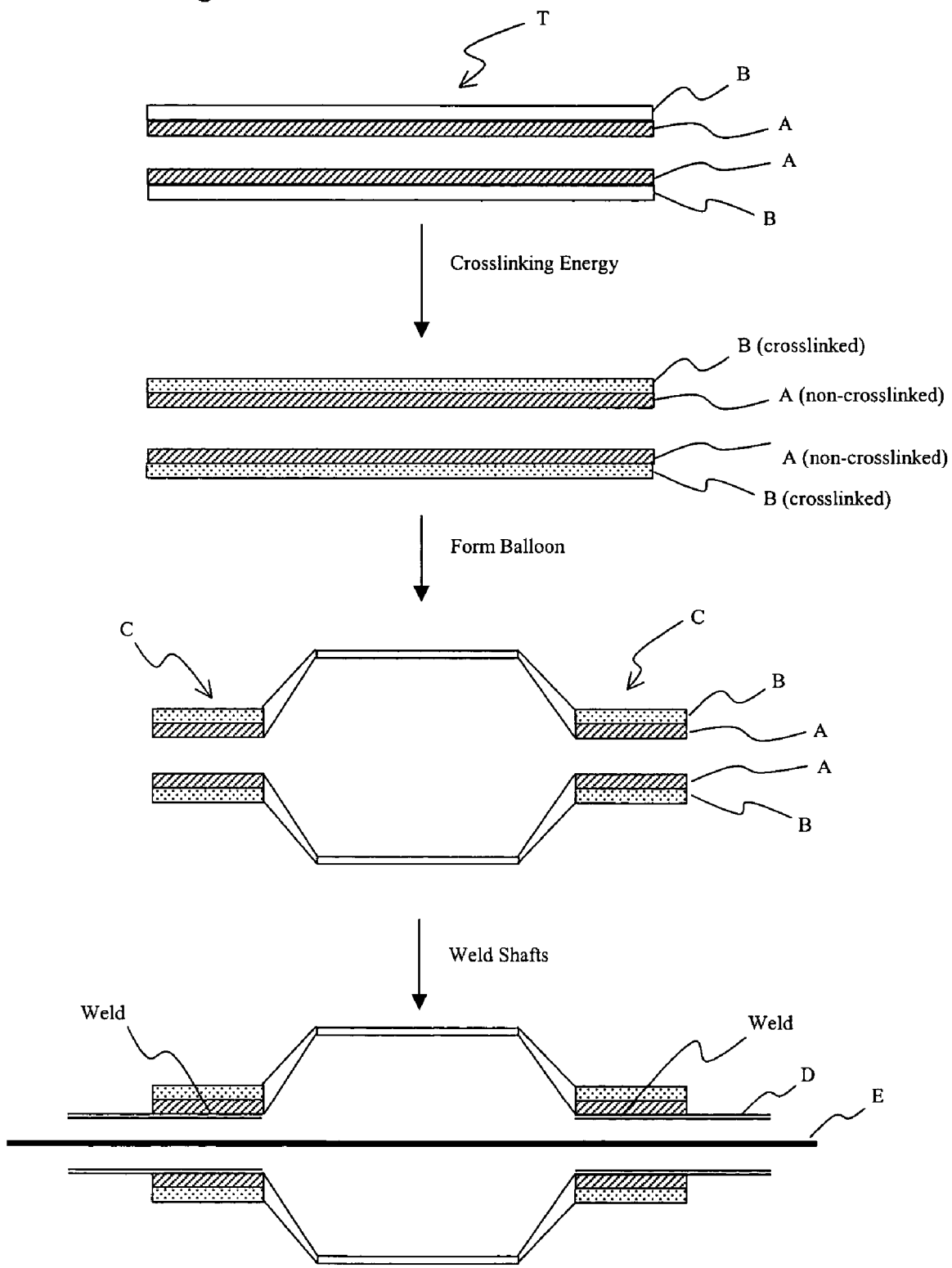

REDUCED PROFILE MEDICAL BALLOON ELEMENT

This patent application claims priority to U.S. provisional application with Ser. No. 60/420,735, which was filed Oct. 24, 2002, and is a continuation-in-part of allowed U.S. patent application Ser. No. 09/558,355 entitled "Dilation Device of Uniform Diameter" that was filed on Apr. 26, 2000, now U.S. Pat. No. 6,656,550 which is a continuation-in-part of U.S. patent application Ser. No. 08/947,000 entitled "Irradiation Conversion of Thermoplastic to Thermoset Polymers" that was filed on Oct. 8, 1997, now U.S. Pat. No. 6,596,818, which is a continuation-in-part of commonly owned U.S. patent application Ser. No. 08/727,145 filed on Oct. 8, 1996, now U.S. Pat. No. 5,900,444. U.S. patent application Ser. Nos. 08/947,000, 09/558,355, U.S. Pat. No. 5,900,444, and all priority applications listed above are incorporated herein by reference in their entirety.

This invention was made, in part, with government support under contract number 1 R43 HL 68331-01, awarded by the National Institutes of Health. The government has certain rights in the invention.

FIELD OF THE INVENTION

The present invention generally relates to balloons for medical devices such as medical or surgical balloons and the catheters incorporating them designed for use in angioplasty, valvuloplasty, gall bladder procedures, neurologic interventions, urological operations and the like. More specifically, the present invention relates generally to angioplasty balloons used for dilating a lesion, obstruction, or stenosis in a blood vessel or the deployment of a stent therein. In particular, the invention relates specifically to balloons comprising polymers that have the attribute of memory or are crosslinked to impart memory as well as to processes for preparing crosslinkable polymers and joining crosslinked balloons to catheter systems. This invention also relates to balloons that have a customizable compliance curve and methods that may be employed to form such balloons. It also relates to shrunk balloons that exhibit a low profile relative to their unshrunk profile. It also relates to an expansive element within a tube whose outer diameter is equal to the outer diameter of the tube from which it was made.

BACKGROUND OF THE INVENTION

Angioplasty, an accepted and well known medical practice, involves inserting a catheter containing an uninflated balloon at or near its distal tip into a blood vessel of a patient, and maneuvering the balloon via the catheter through the patient's vessels to the site of a lesion, obstruction, or stenosis. Typically, a physician fluoroscopically guides the catheter fitted with its expandable balloon, from an entry point at the femoral artery, through a patient's arterial system to the site of the stenosis or occlusion. The uninflated balloon portion of the catheter is located within the blood vessel so that it is centered across a lesion, obstruction, stenosis or reduced area. A pressurized inflation fluid is then metered to the uninflated balloon through a lumen in the catheter in order to expand the balloon and thereby dilate the lesion, obstruction, stenosis or restricted area. The inflation fluid is generally a liquid and is applied at relatively high pressure, usually in the area of six to twenty atmospheres. As the balloon is inflated it expands and forces open the previously closed, stenotic or restricted area of the blood vessel. The dilated artery reestablishes an acceptable blood flow through the artery without resorting to more serious, invasive surgical procedures such as grafts or bypasses.

In 1977 the first human coronary balloon angioplasty was performed by Dr. Andreas Gruentzig. This marked the historical beginning of routine clinical use of Percutaneous Transluminal Angioplasty (PCTA). In 1982, one of the earliest patents for an over the wire balloon catheter, U.S. Pat. No. 4,323,071, to Simpson et al., was issued. By 2001 almost two million angioplasties were reportedly performed worldwide, with an estimated increase of 8% annually. The year 2002 marked the 25th anniversary of the first angioplasty performed in an awake patient.

A wide variety of angioplasty balloon and catheter patents are methods are known. References disclosing angioplasty balloons and catheters include:

| U.S. Pat. No.: | | |
|---|---|---|
| 4,154,244 | May, 1979 | Becker et al. |
| 4,254,774 | Mar., 1981 | Boretos. |
| 4,331,786 | May, 1982 | Foy et al. |
| 4,332,920 | Jun., 1982 | Foy et al. |
| 4,385,635 | May, 1983 | Ruiz. |
| 4,413,989 | Nov., 1983 | Schejeldahl et al. |
| 4,490,421 | Dec., 1984 | Levy. |
| 4,563,181 | Jan., 1986 | Wijayarathna et al. |
| 4,675,361 | Jun., 1987 | Ward, Jr. |
| 4,786,556 | Nov., 1988 | Hu et al. |
| 4,820,270 | Apr., 1989 | Hardcastle et al. |
| 4,886,506 | Dec., 1989 | Lovegren. |
| 4,898,591 | Feb., 1990 | Jang et al. |
| 4,906,244 | Mar., 1990 | Pinchuk et al. |
| 4,917,667 | Apr., 1990 | Jackson. |
| 4,938,676 | Jul., 1990 | Jackowski et al. |
| 4,950,239 | Aug., 1990 | Gahara et al. |
| 4,950,257 | Aug., 1990 | Hibbs et al. |
| 4,952,357 | Aug., 1990 | Euteneuer. |
| 4,964,853 | Oct., 1990 | Sugiyama et al. |
| 4,994,032 | Feb., 1991 | Sugiyama et al. |
| 5,108,415 | Apr., 1992 | Pinchuk et al. |
| 5,156,612 | Oct., 1992 | Pinchuk et al. |
| 5,226,880 | Jul., 1993 | Martin. |
| 5,236,659 | Aug., 1993 | Pinchuk et al. |
| 5,246,420 | Sep., 1993 | Kraus et al. |
| 5,250,069 | Oct., 1993 | Nobuyoshi et al. |
| 5,264,260 | Nov., 1993 | Saab. |
| 5,281,677 | Jan., 1994 | Onwunaka et al. |
| 5,290,306 | Mar., 1994 | Trotta et al. |
| 5,295,978 | Mar., 1994 | Fan et al. |
| 5,300,048 | Apr., 1994 | Drewes, Jr. et al. |
| 5,304,134 | Apr., 1994 | Kraus et al. |
| 5,304,135 | Apr., 1994 | Shonk. |
| 5,304,197 | Apr., 1994 | Pinchuk et al. |
| 5,304,340 | Apr., 1994 | Downey. |
| 5,328,468 | Jul., 1994 | Kaneko et al. |
| 5,334,148 | Aug., 1994 | Martin. |
| 5,335,675 | Aug., 1994 | Wheeler, et al. |
| 5,342,386 | Aug., 1994 | Trotta. |
| 5,344,400 | Sep., 1994 | Kaneko et al. |
| 5,348,538 | Sep., 1994 | Wang et al. |
| 5,358,486 | Oct., 1994 | Saab. |
| 5,397,306 | Mar., 1995 | Nobuyoshi et al. |
| 5,433,713 | Jul., 1995 | Trotta. |
| 5,500,180 | Mar., 1996 | Anderson et al. |
| 5,545,133 | Aug., 1996 | Burns et al. |
| 5,554,120 | Sep., 1996 | Chen et al. |
| 5,556,383 | Sep., 1996 | Wang et al. |
| 5,565,523 | Oct., 1996 | Chen et al. |
| 5,747,591 | May, 1998 | Chen et al. |
| 5,830,182 | Nov., 1998 | Wang et al. |
| 5,849,846 | Dec., 1998 | Chen et al. |
| 5,879,369 | Mar., 1999 | Ishida |
| 5,921,957 | Jul., 1999 | Killion et al. |
| 6,200,290 | Mar., 2001 | Burgmeier |

| Foreign patents and Applications: | | |
|---|---|---|
| 697219 A2 | Feb., 1983 | EP. |
| 117093 A3 | Aug., 1984 | EP. |
| 274411 A2 | Jul., 1988 | EP. |
| 513459 A1 | Nov., 1992 | EP. |
| 537069 A1 | Apr., 1993 | EP. |
| 540858 A1 | May, 1993 | EP. |
| 420488 B1 | Jul., 1993 | EP. |
| 566755 A1 | Oct., 1993 | EP. |
| 592885 A2 | Apr., 1994 | EP. |
| 2651681 | Feb., 1983 | FR. |
| 58-188463 | Nov., 1983 | JP. |
| 8401513 | Apr., 1984 | WO. |
| 9001345 | Feb., 1990 | WO. |
| 9208512 | May, 1992 | WO. |
| 9219316 | Nov., 1992 | WO. |
| 9523619 | Sep., 1995 | WO. | carrying a balloon capable of dilating at a substantially higher pressure to drive the stent into the vessel wall, thereby to assure that there is no risk of the stent later shifting its position and to reduce the occurrence of restenosis or thrombus formation. This "retouch" dilation is often considered necessary when the balloon used to seat the stent is made of a compliant material because such balloons generally cannot be safely pressurized above 9-12 atm., and higher pressures are generally considered necessary to assure full uniform lesion dilation and seating of the stent. In some instances, the same stent-deploying catheter is used to predilate, deploy and seat the stent. Actually this latter situation would be ideal, reducing expense and trauma to the patient.

A wide variety of stent configurations and deployment methods are known. References disclosing stent devices and deployment catheters include:

| U.S. Pat. No. 4,733,665 | Palmaz | U.S. Pat. No. 4,681,110 | Wiktor |
|---|---|---|---|
| U.S. Pat. No. 4,776,337 | Palmaz | U.S. Pat. No. 4,800,882 | Gianturco |
| U.S. Pat. No. 5,195,984 | Schatz | U.S. Pat. No. 4,830,003 | Wolff et al |
| U.S. Pat. No. 5,234,457 | Andersen | U.S. Pat. No. 4,856,516 | Hillstead |
| U.S. Pat. No. 5,116,360 | Pinchuck et al | U.S. Pat. No. 4,922,905 | Strecker |
| U.S. Pat. No. 5,116,318 | Hillstead | U.S. Pat. No. 4,886,062 | Wiktor |
| U.S. Pat. No. 4,649,922 | Wiktor | U.S. Pat. No. 4,907,336 | Gianturco |
| U.S. Pat. No. 4,655,771 | Wallsten | U.S. Pat. No. 4,913,141 | Hillstead |
| U.S. Pat. No. 5,089,006 | Stiles | U.S. Pat. No. 5,092,877 | Pinchuk |
| U.S. Pat. No. 5,007,926 | Derbyshire | U.S. Pat. No. 5,123,917 | Lee |
| U.S. Pat. No. 4,705,517 | DiPisa, Jr. | U.S. Pat. No. 5,116,309 | Coll |
| U.S. Pat. No. 4,740,207 | Kreamer | U.S. Pat. No. 5,122,154 | Rhodes |
| U.S. Pat. No. 4,877,030 | Beck et al | U.S. Pat. No. 5,133,732 | Wiktor |
| U.S. Pat. No. 5,108,417 | Sawyer | U.S. Pat. No. 5,135,536 | Hillstead |
| U.S. Pat. No. 4,923,464 | DiPisa, Jr. | U.S. Pat. No. 5,282,824 | Gianturco |
| U.S. Pat. No. 5,078,726 | Kreamer | U.S. Pat. No. 5,292,331 | Boneau |
| U.S. Pat. No. 5,171,262 | MacGregor | U.S. Pat. No. 5,035,706 | Gianturco et al |
| U.S. Pat. No. 5,059,211 | Stack et al | U.S. Pat. No. 5,041,126 | Gianturco |
| U.S. Pat. No. 5,104,399 | Lazarus | U.S. Pat. No. 5,061,275 | Wallsten et al |
| U.S. Pat. No. 5,104,404 | Wolff | U.S. Pat. No. 5,064,435 | Porter |
| U.S. Pat. No. 5,019,090 | Pinchuk | U.S. Pat. No. 5,092,841 | Spears |
| U.S. Pat. No. 4,954,126 | Wallsten | U.S. Pat. No. 5,108,416 | Ryan et al |
| U.S. Pat. No. 4,994,071 | MacGregor | U.S. Pat. No. 4,990,151 | Wallsten |
| U.S. Pat. No. 4,580,568 | Gianturco | U.S. Pat. No. 4,990,155 | Wilkoff |
| U.S. Pat. No. 4,969,890 | Sugita et al | U.S. Pat. No. 5,147,385 | Beck et al |
| U.S. Pat. No. 4,795,458 | Regan | U.S. Pat. No. 5,163,952 | Froix |
| U.S. Pat. No. 4,760,849 | Kropf | U.S. Pat. No. 5,192,297 | Hull |

The first use of coronary stents in humans was reported in about 1987. By about 1993, the use of a catheter delivered stent to prevent a dilated vessel from reclosing or to reinforce a weakened vessel segment, such as an aneurysm, had become common. A typical procedure for stent installation involves performing an initial balloon angioplasty to open the vessel to a predetermined diameter, removal of the angioplasty balloon catheter, followed by insertion of a delivery catheter carrying the stent and a stent deploying mechanism. The stent is then centered across the opened lesion and then expanded to bring it into contact with the vessel wall by using a balloon as the stent deploying mechanism. The balloon is deflated and the delivery catheter is then removed. The stent deploying balloon is usually larger than the balloon of the predilation catheter. In many cases it has become the practice to then "retouch" the dilation by deploying a third catheter Currently drug-eluting stents hold out the promise of dramatically reducing the occurrence of restenosis or the reclosing of balloon dilated arteries. For example refer to U.S. Pat. No. 6,429,232 to Kinsella, et al.

Balloons used in angioplasty procedures are generally fabricated by molding and have predetermined design dimensions such as length, wall thickness and nominal diameter. Balloon catheters come in a large range of sizes and must be suitably dimensioned for their intended use.

Each kind and size of angioplasty balloon has its own expansion characteristics. This expansion characteristic is a factor of both the wall thickness and the material from which the balloon is molded. If the diameter of a balloon is measured during inflation, and the diameter is plotted, as one coordinate, against the inflation pressure as the other coordinate, the resulting curve is called the compliance curve for that particular balloon. It should also be noted that desirable compliance curves are usually linear straight lines. The prior art discloses balloon catheters and methods for making balloon catheters in which the balloons have linear compliance curves. Reference may be had to U.S. Pat. No. 4,490,421 and U.S. Reissue patent U.S. Pat. No. Re. 32,983 and U.S. Pat. No. Re. 33,561 for disclosures of methods for making balloon catheters having linear compliance curves.

If a balloon is made of a material that results in a relatively large increase in diameter when the balloon is inflated to its expanded diameter, such a balloon is said to be a "high-compliant balloon", "compliant balloon", "balloon with a high compliance curve", or "balloon made from compliant plastic material".

If a balloon is made of a material that results in a relatively small increase in diameter when the balloon is inflated to its expanded diameter, such a balloon is said to be a "non-compliant balloon", a "balloon made from non compliant plastic material' or a "balloon with a low compliance curve.

It should be noted that balloons having compliancy curves anywhere between the "high-compliant" and the "non-compliant curves" are available and are generally termed "semi-compliant".

As typically referred, "non-compliant" balloons are the least elastic angioplasty balloons, increasing in diameter about 2-7%, typically about 5%, as the balloon is pressurized from a inflation pressure of about 6 atm to a pressure of about 12 atm. "Semi-compliant" balloons have somewhat greater elasticity, generally inflating 7-16% and typically 10-12% over the same pressurization range. "Compliant" balloons are still more elastic, inflating generally in the range of 16-40% and typically about 21% over the same pressure range.

All angioplasty balloons have a minimum pressure at which they will burst called the burst pressure. In use a physician is aware of the minimum burst pressure and usually avoids inflating a balloon to the point where it bursts. The burst pressure is determined primarily by the strength of the polymer material from which the balloon is constructed. It should be noted that for a given material, the burst pressure is generally determined by the balloon wall thickness, all other factors being equal.

The strength of polymer materials used in balloon manufacture varies widely. Usually the most inelastic (non-compliant) balloons are also the strongest, being made of highly orientable polymers such as polypropylene, polyethylene terephthalate or other phthalate polyesters or copolyesters, nylons, polyimides, thermoplastic polyimides, polyamides, polyesters, polycarbonates, polyphenylene sulfides, and rigid polyurethanes. "Non-compliant balloons" made from poly (ethylene terephthalate) are commonly referred to as PET balloons. See, U.S. Pat. No. 32,983 to Levy that describes a biaxially oriented, non-compliant polyethylene terephthalate homopolymer (PET) balloon. In addition to PET, other types of materials have been used to produce non-distensible balloons. See, for example, U.S. Pat. Nos. 4,938,676 and 4,906, 244 that report using a biaxially oriented nylon or polyamide material, U.S. Pat. Nos. 4,884,573 and 4,952,357 that report using a polyimide material and U.S. Pat. No. 4,950,239 that reports using a polyurethane material. Non-compliant balloons can be characterized as being somewhat in the nature of paper bags that, once inflated to generally remove folding wrinkles, do not further inflate to any significant degree. The higher tensile strengths of nondistensible balloon materials are generally a result of orienting the balloon material during manufacture of the balloon. These materials may have burst pressures that exceed 20 atmospheres (300 psi).

As a general rule, as compliance increases the strength and hence burst pressure of a balloon decreases. Semi-compliant and compliant balloons made of less highly orientable polymers such as thermoplastic elastomers, polyethylene (high density, low density, intermediate density, linear low density), polyesters, polyurethanes, polycarbonates, polyamides, polyvinyl chloride, acrylonitrile-butadiene-styrene copolymers, polyether-polyester copolymers, and polyether-polyamide copolymers, ethylene-vinyl acetate, olefin copolymers, ionomer resins or blends of these materials, have lower strength than those made from the highly orientable polymers such as PET. Their burst pressure might be in the range of 9-10 atm. See, for example, U.S. Pat. No. 4,154,244 to Becker et al. that describes a high compliant thermoplastic rubber balloon. Balloons with a compliance somewhere between "high" and "non-compliant" can be made of nylon or nylon elastomer materials such as Pebax, polyester elastomer materials such as Hytrel or Arnitel or Pelprene, or Thermoplastic polyurethane materials such as Pellethane. Reference to U.S. Pat. No. 5,951,941, by Wang et al, discloses block copolymer elastomer catheter balloons of nylon elastomers and polyester elastomers. See US 2002/0087165 A1 to Lee et al for balloons of thermoplastic polyurethane materials.

While balloons made of non-compliant materials generally possess relatively high tensile strength values, which is a desirable attribute, especially for dilating tough lesions, they may be subject to disadvantageous properties which compromise their utility. For example, PET balloon in particular have been found to be subject to development of pinholes, are fragile and easily damaged during routine handling, and may develop extensive wrinkles when the balloon is sterilized. Furthermore, PET balloon materials do not readily take a fold or a crease. As such when these balloons are collapsed in a deflated state the collapsed balloon flattens and provides an undesired "winged" profile. The phenomenon of "winging" results when the flat, lateral portions of the deflated balloon project laterally outward beyond the rest of the catheter. A "winged" balloon presents a profile having rigid edges that has a much higher likelihood of injuring the arterial system during placement or withdrawal of the balloon. In addition, materials such as PET do not readily accept coating with drugs or lubricants, which can be desirable in many applications. PET is also difficult to fuse, whether by heating or with known biocompatible adhesives. PET and similar non-compliant balloons tend to be stiff, making the dilatation catheter more difficult to maneuver within tortuous vessels. A non-compliant balloon sometimes requires that a physician has to withdraw and replace a balloon that proves to be smaller than needed to fully dilate the artery. Additionally, the use of non-compliant balloons has been considered to be advantageous because they will not inflate significantly beyond their respective designated dilation diameters, thereby minimizing possible damage to vessels due to over-inflation errors. However, assessment of the artery's size can be miscalculated, or arteries may not be uniform and may taper, or may not coincide with readily available catheter balloon dimensions, leaving only the option of withdrawing the non compliant catheter and inserting another more properly sized catheter.

Compliant or semi complaint balloons can provide a wider range of effective inflation or dilation diameters for each particular balloon size because the inflated working profile of the balloon, once achieved, can be further expanded in order to effect additional dilation. Non-Compliant balloons are typically available in size increments of 0.25 mm while High-Compliant balloons typically have size increments of 0.50 mm. This gives the physician some margin of error in matching a specifically sized balloon with the size of the vessel at the stenosis site. An off-sized artery (i.e. 2.90 mm), which is difficult to dilate with a Non-Compliant balloon, can be dilated with a semi compliant or compliant balloon. Thus, fewer models of High-Compliant balloons are required to fill a range of sizes. Another advantage of a High-Compliant balloon over a Non-Compliant balloon is that if a restriction, after being dilated to its desired diameter, recoils when the balloon is deflated, the High-Compliant balloon can be re-inflated to a higher pressure thus dilating the restriction to a diameter greater than its desired diameter resulting in a satisfactory post recoil lumen diameter. This process can be repeated until the restriction retains its desired diameter after deflation of the balloon. High-Compliant balloons also have disadvantages, for example they cannot be successfully used to dilate a hard lesion. Also if a High-Compliant balloon is located across a restriction and an end or both ends of the balloon extend into non restricted areas, when high pressure is applied to the balloon, the pressure may not be sufficient to crack or dilate the restrict area but will dilate the non-restricted area to diameters greater than their normal diameter. In this situation damage can be done to the non-restricted portions of the vessel. Also "high compliant" balloons usually can not reach the high pressures of "non compliant" balloons. The comparatively lower tensile strength of a compliant or semi compliant balloon may increase the risk of possible balloon failure if the balloon is over pressurized. Compliant balloons having high expansion properties also present the risk that a blood vessel may be damaged or ruptured due to uncontrolled overinflation. This is because the expansion at high pressure of many compliant balloons tends to increase in a non-linear manner thereby increasing the risk of uncontrolled overinflation. Manufacturers attempt to cope with lower burst properties and the overinflation risk by increasing balloon wall thickness. Said thicker wall thickness however results in a larger profile and perhaps stiffer catheter thereby reducing its desirability for certain applications.

The particular distension and maximum pressure attributes of a balloon are influenced not only by polymer type but also by the conditions under which the balloon is blown. Angioplasty balloons are conventionally made by blow molding a tube of polymer material at a temperature above its glass transition temperature. For any given balloon material, there will be a range of distensions achievable depending on the conditions chosen for the blowing of the balloon. For example by controlling blowing conditions such as initial dimensions of tubing, pre-stretch, hoop ratio and heat set conditions, one can vary the compliance characteristics and wall strength of a balloon to some degree. In U.S. Pat. No. 6,110,142 to Pinchuck there are described balloons of nylon that exhibit variable characteristics depending on how they are blown. The data in the reference show that compliance characteristics can be obtained ranging from non-compliant to semi-compliant characteristics and that wall strengths of greater than 15,000 psi can be obtained. According to the author, the balloons exhibit the ability to be "tailored" to have expansion properties that are desired for a particular end use. However, the degree of "tailorability" is limited according to the disclosures to an expansion of at most 35 or 40%.

Due to the limitations inherent in current balloon technology discussed above, it would be desirable to have a balloon catheter which exhibits the wide expansion characteristics of a compliant balloon, but is capable of operating at a high pressure similar to a non compliant balloon, but without the danger of overinflation.

Compliance curves of angioplasty balloons, in their usable range are linear, that is essentially a straight line. As a result a physicians choice, in the past, has been to select a balloon having a linear compliance curve that best meets his needs. Sometimes, Physicians encounter medical situations where an angioplasty balloon having a nonlinear compliance curve is desired. For example a physician may have a medical situation in which he desires a balloon that will during the initial inflation phase increase in diameter by 20% and then in the secondary inflation phase become very rigid and hard with little further increase in diameter. Another example might be the situation where two lesions are encountered, one that can be treated with a High-Compliant balloon and the other that requires a Non-Compliant balloon. Using two balloon catheters in such a situation, which the initial High-Compliant balloon must be removed and replaced with a Non-Compliant balloon, has the disadvantage exposing the patient to the trauma of removing and replacing a balloon catheter, a longer procedure time, and the expense of two balloon catheters. These disadvantages can be avoided by use of a balloon catheter that has a nonlinear or hybrid compliance curve.

In U.S. Pat. Nos. 5,348,538; 5,403,340; and 5,500,181 to Wang et al, there is described a single layer balloon which follows a stepped compliance curve. The stepped compliance curves of said balloon has a lower pressure segment following a first generally linear profile, a transition region, typically in the 8-14 atm range, during which the balloon rapidly expands yielding inelastically, and a higher pressure region in which the balloon expands along a generally linear, low compliance curve. It is claimed that the stepped compliance curve allows a physician to dilate different sized lesions without using multiple balloon catheters. In U.S. Pat. No. 5,490,838 to Miller, there is disclosed a balloon catheter which can be expanded in a stepped fashion to two different known, work hardened diameters. In U.S. Pat. Nos. 6,290,485; and 6,402,778; there is disclosed a method for installing a stent using a single balloon catheter with a stepped compliance curve. Claimed is a single stent deploying catheter for both low pressure predilation and subsequent high pressure embedding of the stent in the vessel wall. However the devices disclosed involve dilation catheters with relatively thick walled balloons, thereby limiting their utility in many applications. For example, in Wang, the stepped compliance curve is obtained by an unusual annealing technique. The entire balloon catheter is submerged in water or air at a temperature in the range of 25-100 degree Centigrade for 3-180 minutes, the temperature and time required in this annealing process, depending upon the size of the balloon that is being processed. This annealing process causes the length and the diameter of the balloon to decrease and the wall thickness to increase which results in a balloon catheter with a hybrid compliance curve. The relatively thick wall balloon of Wang results from allowing the balloon to shrink both axially and radially.

It would be desirable to have or be able to manufacture a series of improved medical dilation catheters for angioplasty, stent deployment or other usages containing a dilation element with linear or non linear expansion characteristics, and/or with higher compliance characteristics and/or with reduced risk of overinflation at high pressure and/or a balloon element of whose profile is the same as the tube from which it was formed.

Thus fabricating an angioplasty balloon places conflicting demands on the materials used to obtain extremely thin walled high strength relatively inelastic balloons of predictable and desirable inflation properties. These conflicting demands usually result in a trade off of properties with certain characteristics being balanced against others. For example, a minimum balloon profile is advantageous because it allows the balloon to easily reach and then traverse tight stenosis or occlusions with minimum trauma to arterial vessels. This requires a thin walled balloon that tends to lower the burst pressure of the balloon. In order to maintain the higher burst pressure of a balloon in order to push open a stenosis easily, a very high strength material must be used so the thin wall will not burst under the high internal pressures necessary to accomplish this task. But high strength materials tend to be fragile, stiff and very inelastic. However, it its desirable that the balloon be flexible and have some elasticity so that the inflated diameter can be controlled, and to allow the surgeon to vary the balloon's diameter as required to treat individual lesions, yet still be able to compensate for variations in vessel walls or "recoil" as well as be maneuverable through tortuous vessels. However, elasticity must be relatively low to avoid overinflation and damage to the vessel. In addition the diameter must easily controllable with pressure so that small variations in pressure will not cause wide variation in diameter.

Medical balloons typically retain their shape when in the unpressurized state somewhat like a collapsed paper bag. In order to maintain a low crossing profile, the collapsed balloon must be wrapped tightly around itself. The current art allows a minimum balloon profile by minimizing the wall thickness of the balloon material. This allows for a low profile by enabling a collapsed balloon to be wrapped around itself multiple times without appreciably increasing the diameter of the area contained the collapsed wrapped balloon. But the thinner wall gives a weaker balloon and thus reduces the amount of pressure that can safely be used to inflate the balloon and open a stenosis. This requires the use of very strong materials to allow for the required minimum balloon wall thickness and usually yields a rigid, hard, stiff balloon. Use of a more elastomeric material that tend to be flexible, soft and deformable yields either a weaker balloon, which may overinflate and damage the vessel or burst at too low a pressure, or a thicker balloon which presents an unacceptable profile.

The design of a balloon therefore is a compromise and it was thought unlikely to obtain a high compliant, high-pressure balloon, flexible, low profile balloon with a linear or non-linear compliance curve within a single balloon. Therefore, there is still a need for improved materials and method for inflatable medical balloon elements.

SUMMARY OF THE INVENTION

In accordance with a preferred embodiment of the present invention, a polymer material is first extruded or otherwise formed into a continuous tube of a desired length and outside and inside diameter. The type of polymer is chosen based on the requirements of the device to be manufactured, and one or more of the following characteristics: its ability to be crosslinked, and/or its ability to exhibit "shrink memory."

As stated above, the dilatation device of the present invention is suitably fabricated from a polymer material, preferably a thermoplastic. A wide variety of polymers may be used in accordance with the present invention, including thermoplastic polymers and thermoplastic elastomer polymers such as polyamide elastomer polymers, polyester elastomer polymers, polystyrene elastomer polymers, thermoplastic polyurethane elastomer polymers, and blends of rubber and thermoplastic polymers. These materials can be formed into tubes, optionally crosslinked, and subsequently molded to form balloons. Crosslinking, if utilized, may be imparted preferably by exposing the polymer tube to energy such as heat, light, radiation, high-energy electron beams, gamma rays, UV light, infrared radiation or combinations thereof. Often, a functional material or co-agent must be added to the polymer in order to render it crosslinkable. Shrink memory may be imparted by stretching the polymer tube or crosslinking the polymer tube by using energy such as heat, light or radiation, high-energy electron beams, gamma rays, UV light, infrared radiation or combinations thereof.

A non-limiting embodiment of the present invention is a polymer material that is first extruded or otherwise formed into a continuous tube of a desired length and outside and inside diameter and crosslinked by a suitable method. A length of the tube is suitably utilized to form a balloon by heating a portion of the tube in a mold, stretching and applying pressure to the interior of the tube to expand the heated, stretched portion. Stretching before or while blowing the balloon results in axial orientation of the polymer in the balloon along with radial orientation (known in the art as biaxial orientation) and improves the balloon burst strength. A tube with a "balloon" of a specified outer diameter, wall thickness, and length, results. The wall thickness of the balloon is less than the wall thickness of unexpanded portion of the original tube.

The balloon is removed from the mold after cooling the mold and releasing the interior pressure. The resulting optionally crosslinked balloon may be used as is, to yield a balloon with an improved compliance profile.

Alternatively, the portion of the tube containing the balloon is then reheated at or to a certain temperature while restraining the tube ends so that axial balloon contraction is restricted in a controlled manner. This controlled re-heating will cause the formed balloon to shrink, due to "memory", to some outer dimension which will be less than the outer dimension of the balloon before applying the controlled re-heating, and whose length will in one embodiment be unshrunk. The exact outer diameter of the shrunk balloon is determined by the length of time and shrink temperature that heat is applied to the balloon containing "memory". The higher the shrink temperature and the longer the shrink time, the greater the shrinkage, and the more closely the shrunken balloon diameter will approximate the outer diameter of the tube from which it was formed. By judicious application of combinations of shrink temperature and shrink time, the balloon may be shrunk to any size between the unshrunk balloon diameter and the original diameter of the tubing from which it was constructed. A wall thickness of the shrunken balloon will be associated with a given shrunken balloon diameter. The greater the shrinkage the greater the degree to which the wall thickness will tend to increase relative to the unshrunk balloon wall thickness. However the increase in wall thickness can be controlled by restraining the ends of the tube while the balloon is heated for the purpose of shrinking. While the shrink temperature and shrink time is being applied, the ends of the tube are suitably restrained by being subjected to one of the following restraining alternatives. The tube ends may be restrained so as to maintain the same original overall length that the tube exhibited with the formed balloon still in place. Alternatively, the tube ends may be longitudinally elongated while the shrink temperature and shrink time is being applied, preferably to a predetermined length. In a least preferred alternative, the balloon may be allowed to longitudinally contract in a controlled manner. However, this will result in a thickening of the shrunk balloon wall to a greater extent than in the more preferred alternatives. This will yield a balloon element with a reduced profile, as well as an altered compliance curve relative to the unshrunk balloon profile and compliance curve. In an extreme application of the least preferred alternative, the balloon would fully contract radially and axially resulting in the original tube being reformed similar to a piece of shrink tubing. This is to be avoided for the purpose of a useful medical balloon, however for the formation of shrink tubing this would be an acceptable consequence.

The application of a suitable combination of shrink temperature and shrink time in combination with the "memory" effect, results in the formation of an expandable portion within a tube. This expandable portion thereby contains a susceptibility to preferably expand upon introduction of pressure to the interior of the tube. The expandability is expressed in a compliance curve wherein the size of the expandable balloon portion varies with the amount of pressure introduced to the interior of the tube. This compliance curve can be a straight linear line or a non-straight non-linear line depending on the combination of the specific material employed, the shrink temperature and the shrink time applied, and the extent to which the balloon shrinks during the process. The tube now is an expandable element that contains an expandable portion and a less expandable portion with the expandable portion usually contained between the less expandable portions, and may be joined to a catheter to complete a medical dilatation device.

It has been found particularly that the addition of certain functional materials may result in undesirable small regions of prematurely crosslinked or otherwise degraded polymer called "gels". Gels are particularly undesirable with respect to balloon catheters, since they form areas of stress concentration or other defects that weaken the wall of the balloon that may cause a premature failure of the balloon by lowering the burst pressure of the balloon. In order to minimize the formation of gels, it was found beneficial to first prepare a concentrate of a functional material in a polymer and then mix or blend the concentrate with a polymer which contains no functional material. The ratio of the amount of unmodified polymer relative to the polymer with high amounts of co-agent is called the let down ratio. Since only the concentrate containing polymer is exposed to multiple heat cycles, this procedure minimizes the amount of polymer exposed to an extra heat history and hence minimizes the formation of gels.

In the construction of balloon catheters, once the balloon element is formed it is necessary to attach it in some manner to the remainder of the catheter assembly. A catheter assembly at the distal end of a catheter assembly generally consists of a larger outer shaft, and a smaller inner shaft, located within the lumen of the outer shaft. The proximal end of the balloon element is attached to the surface of the outer shaft, and the distal end of the balloon is attached to the surface of the distal end of the inner shaft. The preferred method of attachment is to weld the balloon element at the interface of the respective catheter shafts by applying heat and pressure. Welding provides smooth, flexible and strong joints between the component parts. Since the balloon element and the shafts are usually constructed at least in part from a thermoplastic polymeric material, the application of heat and pressure melts the thermoplastic polymeric materials and causes them to bond to each other. In the instance where a balloon element is composed of a crosslinked polymer, the welding cannot be performed since a crosslinked polymer is a thermoset, no longer melts and usually will not bond to the shafts. One embodiment of a means for welding a crosslinked balloon to a catheter shaft would be to weld or otherwise attach lengths of compatible and uncrosslinkable polymer tubing to one or both ends of a length of crosslinkable polymer tubing prior to exposure of the tubing assembly to crosslinking energy. The result would be a length of tubing consisting of a central crosslinkable section with a non-crosslinkable section at one or both outer ends. Upon exposure to crosslinking energy, only the central portion will crosslink, while the outer end or ends will remain uncrosslinked. Thus, after applying crosslinking energy, a tubing assembly will be obtained with a crosslinked area and a noncrosslinked area. The noncrosslinked area would be located at one or both ends of the tubing assembly and would be weldable. In the case where the crosslinked section of tubing is centrally located between two uncrosslinked sections of tubing, said tubing assembly can be utilized to form a crosslinked balloon within the central crosslinked portion of the tubing assembly and thereafter, the balloon may be attached to the balance of the catheter shafts via the uncrosslinked outer ends of said balloon containing tubing assembly. A tube consisting of a polymer material that normally will not crosslink is then preferably butt welded to both ends of tubing that normally will crosslink forming a continuous tubing assembly containing a central crosslinkable section and outer non-crosslinkable sections. Upon exposure of the entire welded assembly to crosslinking energy, only the central portion of the assembly consisting of tubing B will crosslink while the ends of the assembly consisting of tubing A remains uncrosslinked. Thereafter the assembly can be utilized to form a crosslinked balloon from within the central crosslinked portion, while the uncrosslinked section provide weldable ends.

Another embodiment for enabling a crosslinked or thermoset balloon to be welded to a thermoplastic catheter shaft would be to co-extrude or otherwise apply a layer of non crosslinkable polymer to the inner and/or outer surface of a crosslinkable polymer tube during or after the formation of the crosslinkable polymer tube and prior to (or possibly after) exposure of the tubing assembly to crosslinking energy. This would result in a tubing assembly with a non-crosslinkable layer on the inner and/or outer surface of a crosslinkable layer of tubing. When the tubing assembly is exposed to crosslinking energy, only the crosslinkable layer will crosslink, while the uncrosslinkable layer or layers will remain uncrosslinked. One can then utilize the resulting tubing to form a balloon in the manner previously described. Said balloon will comprise at least one layer which will be a crosslinked, and at least one surface which will be uncrosslinked and therefore weldable to the surface of another thermoplastic. For example, a coextruded tube assembly, consisting of an inner layer comprising a thermoplastic polymer material that normally will not crosslink and an outer layer comprising a compatible but crosslinkable material (when exposed to crosslinking energy). The entire co-extruded tubing comprising the outer crosslinkable layer and the inner non crosslinkable layer, is then exposed to crosslinking energy. Only the portion of the tubing consisting of outer layer will crosslink while the inner portion of the tubing consisting will remain uncrosslinked. Since the inner layer remains uncrosslinked and therefore a thermoplastic, it will be weldable to another thermoplastic. The tubing consisting of the crosslinked outer layer, and the thermoplastic inner layer could be utilized to form a balloon as previously described. A balloon with a crosslinked outer layer and a thermoplastic inner layer would result. The ends of the formed balloon could thereafter be placed over a thermoplastic catheter shaft and welded thereto. In summary, if the uncrosslinked, thermoplastic and weldable layer comprises the inner lumen of the ends of the formed balloon element then a weldable tube could be placed with the lumen of the ends of the balloon and welded thereto. Alternatively, if the uncrosslinked, thermoplastic and weldable layer comprises the outer layer of the ends of the formed balloon element then the ends of the balloon element could be placed within the lumen of another fuse weldable tube and welded thereto.

Various objects, features, aspects and advantages of the present invention will become more apparent from the following detailed description of preferred embodiments of the invention.

BRIEF DESCRIPTION OF THE DRAWING

FIG. 1B is a drawing of the steps involved in forming a crosslinkable balloon with a weldable inner surface.

Figure 1:
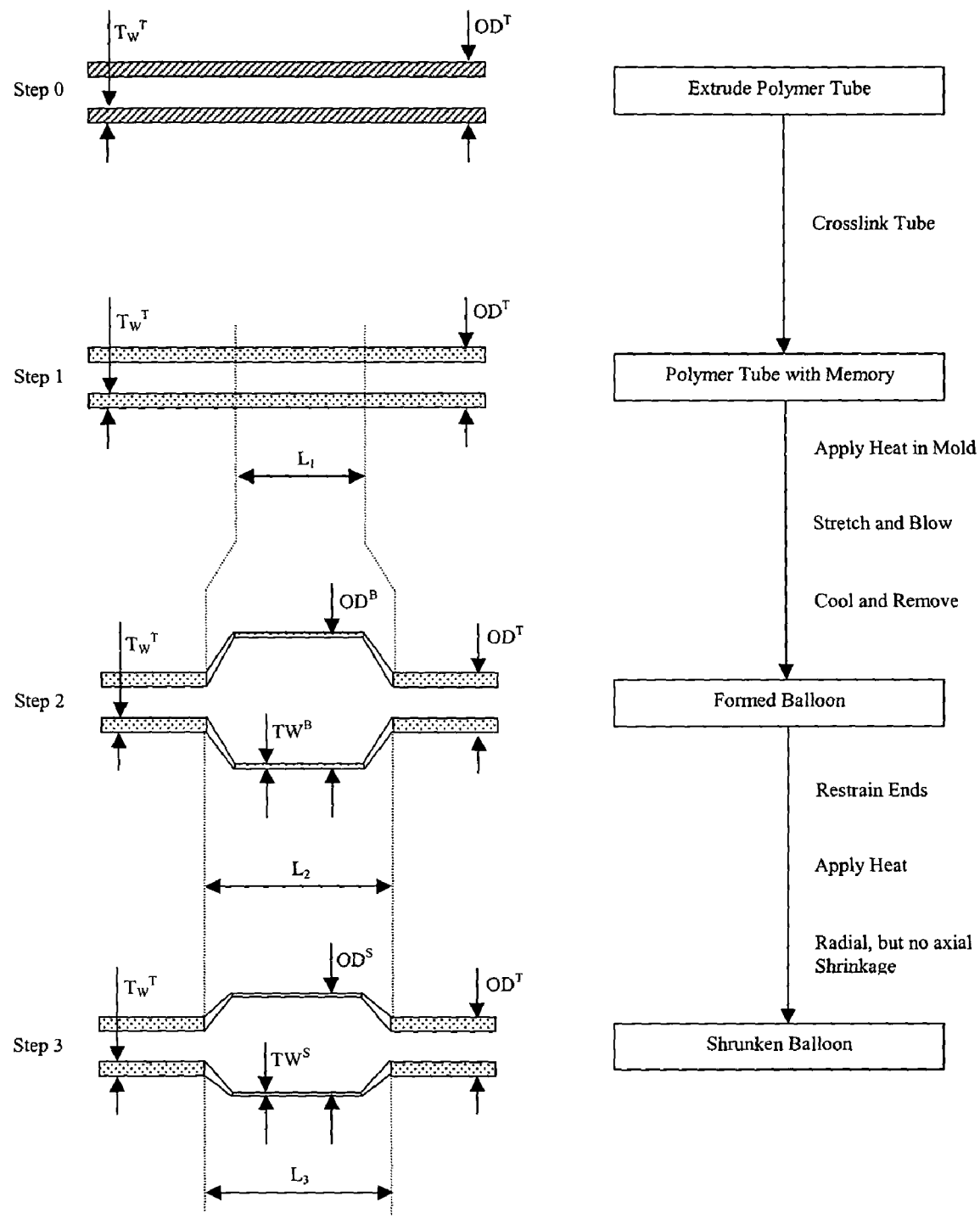
FIG. 1 is drawing of the steps which could be used to form a shrunken medical dilation balloon.

Table 1 lists the elongation of Pebax 7233 at different irradiation dose levels in Megarads.

DETAILED DESCRIPTION

Balloon catheters in general and angioplasty balloon catheters in particular are widely used, especially for treating circulatory problems. Balloons for medical catheters such as angioplasty balloon catheters are usually made by blow molding a thin walled balloon from a portion of a tube made of a relatively inelastic thermoplastic material. The balloon is then deflated, attached to a catheter and then folded around the catheter. In order to allow compact folding of the balloon, and hence a small profile, the wall thickness of the balloon must be thin. However, for a given material, the thinner the wall of the balloon, the lower the burst pressure. Since certain applications, especially coronary angioplasty procedures require balloons capable of expanding at high pressure, strong materials are required for construction of the balloon. Strong materials, allow very thin walled balloons to be constructed that can be inflated to high pressure and will exhibit very high burst pressure. However strong materials tend to be stiff and inelastic which exhibit minimal expansion within their useful pressure range. This necessitates manufacture of a large number of catheters, each properly sized for a specific vessel diameter. In addition, with such low compliance materials, if an undersized catheter is chosen, it must be withdrawn and a new catheter inserted at the cost of increased trauma and higher expense.

Within the present state of the art, the balloon compliance is largely determined by the characteristics of the material selected. Some limited "tailoring" of the balloon compliance can occur by varying certain blow molding parameters. For example, by varying the hoop ratio of the balloon (defined as the ratio of the balloon OD divided by the unblown tube ID), or the heat setting temperature and time, one can effect a change in the balloon compliance curve. However such changes in balloon compliance may involve undesirable changes in other balloon characteristics such as reduced burst strength or increased wall thickness. For example in see U.S. Pat. No. 6,110,142 to Pinchuk et al, for the effect of hoop ratio and heat set temperature on the compliance curves for Nylon (see FIGS. 4 and 5 of that Pinchuk patent). The present invention discloses a method to effect changes in the compliance curve of a material even though the hoop ratio and/or the heat set temperature remains unaltered.

The present invention discloses a novel method of manufacture of a balloon for use on a balloon catheter whose compliance characteristics can be altered by crosslinking the material. In addition the present invention discloses a novel method of manufacture of a balloon for use on a balloon catheter whose compliance characteristics can be customized at the time of manufacture, by shrinking the balloon from its initial molded size, and thereby imparting any one of a wide range of possible compliance curves depending on the manner in which the balloon was shrunken and the needs of the device.

The present invention thereby allows the creation of a balloon catheter with a "customizable" compliance profile. For example, depending on the shrinkage imparted to the balloon from its original formed size, a balloon with linear or non-linear compliance curves could be manufactured in order to exhibit higher compliance as well as high burst pressure. Or, if crosslinked tubing was used to form the balloon, and not shrunk, a balloon could be manufactured with a compliance curve that exhibits reduced tendency to overinflate at high pressure, that is a balloon with a "flatter" (lower or reduced) compliance curve would be result while maintaining acceptable burst pressure. This innovation thereby overcomes limitations of the prior art wherein high compliance balloons are generally of lower burst pressure than low compliance balloons, or wherein certain balloons exhibit a tendency to overinflate at high pressure. In addition this technology allows for reducing the profile of a given size balloon perhaps without requiring the wrapping of a collapsed balloon about itself. In addition this technology allow the formation of a balloon wherein the OD (outside diameter) of the expandable element can be the same OD as the tube from which it is formed. This allows for a practical method for manufacture of "micro" balloon catheters smaller than presently available in the art. In essence then, by forming a balloon, optionally crosslinked, and/or by shrinking of a formed balloon, one could manufacture a wide range of dilation devices whose compliance characteristics vary from high compliant to low compliant, with linear or non-linear curves, or anything in between, all while maintaining desirable burst strength and low to very low crossing profiles.

This invention takes advantage of the "shape memory" characteristic that may be imparted to a wide variety of materials particularly certain thermoplastic polymers ("Thermoplastics"). Thermoplastics are generally polymers that soften or melt when exposed to heat and harden when cooled to room temperature. That is, thermoplastics are capable of being shaped or molded upon the application of heat. Thermoplastics are distinguishable from other 'plastic' materials such as moist clay that do not require the application of heat in order to be shaped or molded.

Shape memory may be imparted to polymers or polymer blends via a number of processes such as, for example, by crosslinking, including the formation of networks or interpenetrating networks, or through stretching or compression of a polymer.

Crosslinking is the bridging of two or more adjacent polymer molecular chains via a chemical bond, usually a covalent bond. The bond involves an element, functional group, or chemical compound, which joins certain carbon or other atoms on one polymer chain to the carbon or other atom on one or more other polymer chains. A covalent bond can be distinguished from a non-covalent bond such as an ionic or hydrogen bond. Non-covalent bonds will usually dissipate upon the application of heat thereby allowing a thermoplastic polymeric material to melt and flow at elevated temperature. In contrast covalent bonds usually do not dissipate upon the application of heat and a thermoplastic polymer crosslinked through covalent bonds usually will not melt or flow at elevated temperature. However, a crosslinked thermoplastic polymer may soften and/or deform at elevated temperatures. In addition, crosslinked thermoplastic polymers may decompose if the temperature is elevated a sufficient amount.

A thermoplastic material can be considered to be a thermoset material once crosslinking occurs. A "Thermoset" material is a general term that can be applied to any material that solidifies or 'sets' irreversibly when exposed to an energy source such as heat. This property is usually associated with covalent crosslinking of the molecular constituents induced by heat or other energy sources such as radiation. Included in the thermoset category are many diverse materials such as rubber, bread, scrambled eggs, and crosslinked thermoplastics. A thermoset plastic has a characteristic such that usually it no longer melts and/or flows upon heating above its crystalline melt temperature ($T_m$). In order to crosslink rubber or a thermoplastic, it may be necessary to add "curing agents" such as organic peroxides or (for rubber) sulfur and/or a crosslinking agent such as a methacrylate monomer.

Even though a crosslinked thermoplastic is technically no longer a thermoplastic but rather a thermoset it may still be possible to form the crosslinked thermoplastic into a new shape at elevated temperature. This feature is used to advantage in forming items that exhibit "shape memory". Polymers, suitable for imparting shape memory, are usually thermoplastic materials, optionally crosslinked, with a crystalline component (or a non crystalline component with a high glass transition temperature-however see U.S. Pat. No. 5,964,744 to Balbierz et al for a shape memory device from a material having a low glass transition temperature).

If a thermoplastic polymer is crosslinked and then heated, usually above its crystalline melt point ($T_m$), stressed, and cooled under stress to below the ($T_m$), the crystals reform. Since the strength of the crystalline regions far exceeds the forces due to the strength of the crosslinks, the polymer stays stressed even though the stressing force has been removed. If heat is applied again, sufficient to melt the crystals, the crystalline regions lose their strength allowing the crosslink forces to dominate. The crosslinks thereby return the material back towards its unstressed shape.

Restated in more general terms, with respect to memory and crosslinking, if a certain polymeric object in a first configuration is crosslinked, then heated, usually above its crystalline melting point ($T_m$), reformed into a second configuration, and cooled below the ($T_m$), it will retain that newly formed second configuration. If it is subsequently reheated to near or above the ($T_m$), the object will tend to revert, due to memory, from the second configuration to the first configuration.

It should be noted that if the second configuration is larger than the first configuration, then the resultant shape memory is a tendency to shrink and is referred to herein as "Shrink Memory".

If the second configuration were smaller than the first configuration, then shape memory would result in expansion rather than shrinkage and the memory is herein referred as "Expansion Memory".

Shrink memory is imparted by stressing the first configuration through some sort of stretching process to form a second configuration that is larger than the first configuration.

Expansion memory is imparted by stressing the first configuration through some sort of compression process to form a second configuration that is smaller than the first configuration.

With respect to shape memory and uncrosslinked polymers, if a polymeric object of a first configuration is heated, preferably above its glass transition temperature but below its crystalline melting point, reformed into a second configuration, and cooled, it will retain that second configuration. However, if it is subsequently reheated, the second configuration will tend to revert somewhat towards the first configuration and is also referred to herein as "Memory". Said "Memory" can be either "Shrink Memory" or "Expansion Memory" depending on whether the second configuration is larger or smaller than the first configuration.

Memory induced by crosslinking polymeric objects tends to be stronger than memory induced in the absence of crosslinking. This means that, for example, a crosslinked object will shrink to a smaller size than a stretched object upon reheating, all other factors being equal. This is because the memory in uncrosslinked materials is dependent on relaxation of molecules that have been oriented by stretching the polymer at a temperature between the glass transition and melt temperature. Smaller recoveries occur since the heat necessary to cause an oriented polymer to shrink causes the some of the polymer chains to slip past each other rather than retract as in the case of a crosslinked material.

A crosslinked polymer however tends to act as an elastic material especially near or above the crystalline melt temperature, the chains do not slip and hence more of the deformation is recoverable upon removal of the stress. This "Memory" effect whether induced by stretching or crosslinking is widely used, for example, in shrink tubing and shrink wrap film.

Expansion memory can be applied in a novel way, for example, for the formation of a medical device such as a self-expanding polymer stent. A tubular polymer member, optionally crosslinked, of suitable size (the first configuration), can be heated and compressed (the second configuration), for example, around a removable mandrel, then cooled to maintain the smaller second configuration. After the optional removal of the mandrel, a tubular member of reduced size with Expansion Memory is obtained. Upon the application of heat, the reduced size tubular member will tend to expand to its larger original size or first configuration. An advantage of this approach, is that via a compression process the tubular polymer member can be compressed in a manner so that the axial dimension is constrained. Thus, in one aspect, the tubular member would be compressed radially, while the axial length would not be decreased. Therefore when it re-expands, it will only re-expand in the radial dimension while the axial dimension will remain constant or nearly so. This feature is important for example in medical stent applications such as coronary stents applications, wherein it is important for the physician practitioner to pre-select the length of the stent to match to length of the lesion or wall to be reinforced. This is in distinction to the polymer stent disclosed in U.S. Pat. No. 6,248,129 to Froix, wherein a stent is imparted elastic memory by a stretching process. This stretching process, which reduces the outer diameter of a tubular polymer member, also lengthens the axial dimension of the device. Therefore when expanded, the device will inherently shrink axially, which as previously mentioned is disadvantageous for medical stent applications.

The present invention also has the advantage that it is stable until activated by the application of sufficient heat or other energy. That is, once compressed, no cover or other restraining device is required to prevent it from re-expanding. This in distinction to other polymer stents which self expand in the manner of a compressed spring and require some sort of restraining device to maintain the device in a compressed state. An example is disclosed in U.S. Pat. No. 4,820,298 to Leveen et al. As disclosed therein, a thermoplastic polymer is formed into a helical coil by providing a linear extrusion and winding the same on a mandrel and reheating to form a helical spring coil. The stent is inserted with a stylet. When the stylet is removed, the stent expands under its recovery memory to assume a helical configuration. This recovery memory is based upon the fact that it was formed from a linear strip and wound onto a mandrel which resulted in stored energy similar to a spring, causing it to expand into a helix when released from the stylet. It is believed that even though such a stent is formed of plastic, it has a number of disadvantages making it unsuitable for use in many applications. It is necessary to mechanically restrain the stent to prevent it from expanding prior to insertion into the vessel. Also it is believed that it is hard to predict the expansion forces exerted when it is released. Another self expanding polymer stent with spring like resiliency is disclosed in U.S. Pat. No. 6,245,103 to Stinson. It also has the disadvantage of requiring the mechanical restraint of the stent to prevent it from expanding prior to insertion into the vessel.

It should be noted that the "reduced size tubular member with expansion memory" of the present invention, if constructed in the form of a hollow cylinder, may comprise walls which may be continuous, or discontinuous. For example, perforations in the wall with openings or holes of various sizes can be provided. These can serve, illustratively, to increase the flexibility of the device to facilitate delivery to locations within the body, such as within the coronary artery system, where tortuous pathways may exist. In addition the tubular member can be in the form of a continuous helix or other structure formed by loops or turns of a linear polymeric material, with a lumen extending throughout.

Such a "reduced size tubular member with expansion memory", if placed within a bodily cavity, such as a coronary artery, and heated or exposed to some energy source, will self expand to a predetermined size, thereby reinforcing the bodily cavity. The reduced size tubular member can be placed within the bodily cavity through the use of a suitable delivery catheter such as a balloon catheter or other means. The "reduced size tubular member with expansion memory" could be heated, or exposed to some energy source via the delivery catheter, for example by circulating a heated fluid through the inner lumen of the catheter or by electrically heating the catheter in the manner disclosed in U.S. Pat. No. 6,123,718 to Tu et al. In one embodiment it is envisioned that natural body heat could the energy source for expansion. In such an eventuality, the "reduced size tubular member with expansion memory", could be cooled by some means such as by circulating a cooling liquid within the lumen of the delivery catheter, until the location is reached where expansion is desired. At that point, the cooling means could be withdrawn or turned off so that the influence of the bodily environment can heat the "reduced size tubular member with expansion memory" thereby allowing it to expand.

If a balloon catheter is utilized as a delivery catheter, the balloon portion could be utilized to assist the expansion of the "reduced size tubular member with expansion memory". Such a combination of balloon catheter and the "reduced size tubular member with expansion memory" might have advantageous properties such as more rapid expansion, or expansion of the tubular member at lower heat energy levels, than a similar "reduced size tubular member with expansion memory" deployed by some other means such as in a delivery catheter with no expansive balloon element. Regardless of the manner of extension, it is generally contemplated that the stent has a substantially continuous outer surface. The term "substantially continuous outer surface" as used herein refers to the outer surface of a tubular element, which may optionally include one or more openings to increase flexibility of the compressed expandable stent. However, the term "substantially continuous outer surface" expressly excludes discontinuous surfaces that are formed from a plurality of segments that exhibit changeable radial curvatures (e.g., as described in U.S. Pat. Nos. 5,603,722 and 5,954,744).

Therefore, a "reduced size tubular member with expansion memory" could also be termed "a self expanding polymer stent". A "self expanding polymer stent" would be useful in numerous medical applications such as stenting of coronary arteries, peripheral arteries, cranial arteries, aortic arteries, biliary ducts, renal ducts, or in any weakened bodily cavity where reinforcement against a tendency to collapse is desirable. It could be made in any size or wall thickness suitable to the intended application.

"Self-expanding polymer stents" might be advantageously employed in place of stents constructed of other materials such as steel possibly due to improved biocompatibility or enhanced ability to deliver a drug. In addition a temporary polymer stent could be constructed of a polymeric materials that is bio-absorbable. Alternatively, a permanent stent could be constructed of a biostable polymer material.

Additionally, this invention applies "Shrink Memory" technology in a novel way, for example, in coronary angioplasty balloon catheter fabrication wherein the availability of a catheter of higher compliance and burst strength yet of low profile would be of great utility to the medical profession. This however does not preclude its use in other medical areas such as in peripheral, or cranial vessels, or other body cavities such as bile ducts or kidney lumens or urethral cavities where similar characteristics in whole or in part might be desirable and useful.

In accordance with one embodiment of the present invention and as depicted in FIG. 1, a polymer material is first extruded or otherwise formed into a continuous tube of a desired length and outside and inside diameter. The type of polymer is chosen based on the requirements of the device to be manufactured and its ability to be crosslinked. In addition the polymer should exhibit "shrink memory". In general, most thermoplastic polymers of sufficient strength for use in angioplasty balloon catheters (or other forms of dilatation devices) are crosslinkable (possibly with the addition of a crosslinking agent) and will exhibit shrink memory to some degree and are therefore are potentially useable in the present invention. Depending on the material, crosslinking may be imparted by using energy such as heat, light or radiation. For example, high-energy electron beams, gamma rays, UV light, infrared radiation or combinations thereof, of sufficient energy dose could be utilized to impart crosslinking. The energy dose required would depend on the energy source, the material being crosslinked and the degree of crosslinking desired. For example the energy dose, for an electron beam energy source, an energy dose in the range of 0.1 to 250 MegaRads is usually sufficient to crosslink most crosslinkable polymer materials. These methods of imparting crosslinking are described as examples only and are not intended to be limiting. A person skilled in the art would recognize that there are many substantially equivalent methods to impart crosslinking. Shrink memory is imparted due to the crosslinking of the polymer tube.

In accordance with a second embodiment of the present invention not depicted, a polymer is first thermoplastically extruded or otherwise formed into a continuous tube of a desired length and outside diameter. Rather than being crosslinkable this type of polymer is chosen based on its ability to be stretch oriented in order to retain a "shrink memory." In general, most thermoplastic orientable polymers of sufficient strength for use in angioplasty balloon catheters (or other forms of dilatation devices) are stretch orientable and will exhibit shrink memory and are therefore useable in the present invention. PET and Nylon are examples of orientable polymers that can be induced to have Shrink Memory. Shrink memory is then imparted during the stretch blow-molding step of forming the balloon. As mentioned above stretch molding is less effective as a method for imparting shrink memory due to the smaller recoveries possible, and for other reasons that will be explained below.

Both embodiments may be combined in the present invention; for example, the crosslinked tube may also be stretched during the balloon forming process.

In the current art, balloons can be formed in balloon blow molding machines or by other methods. Typically in balloon forming, a hollow tube is inserted into a mold and the ends of the tubing secured. The tubing is heated to a designated temperature (molding temperature) for designated time, and the heated tubing is subjected to longitudinal (axial) tension and expanded (stretched) a designated multiple of its length in the axial direction. The heated stretched tubing is then blown into a balloon by applying pressurized nitrogen at a designated pressure. The mold is then cooled to room temperature and the balloon is allowed to set at room temperature in the mold under pressure for a designated time. Thereafter, the system can be depressurized and the balloon removed from the mold. Certain steps can be added or subtracted or modified from the above procedure without significantly departing from the essence of the balloon forming procedure. For example, after forming the balloon in the mold and while the balloon is still under pressure, the balloon could be annealed or heat-treated in the mold for a designated time at a temperature usually higher than the molding temperature. All of the above processes are well known to practitioners of the art of balloon blowing.

For example, a series of Pebax angioplasty balloons were reported formed (in U.S. Pat. No. 6,200,290 to Burgmeier) using the above procedure as follows: A length of tubing was placed in a mold. The section of tubing within the mold was heated in the range of 190-220 deg. F (87-104 deg. C.) for about 25-30 seconds, and the heated tubing was subjected to a longitudinal tension and expanded 1-2 times its length in the axial direction. The stretched tubing was pressurized with nitrogen in the range of about 350-500 psi and heat treated in the mold for about 10-20 seconds at about 260-270 deg. F. (127-132 deg. C.). The mold was then cooled to room temperature and allowed to set at room temperature in the mold under pressure for approximately 10 to 15 seconds. Thereafter, the system was depressurized and the balloon removed from the mold.

The present invention differs from the regular process, by utilizing, thermoplastic tubing, optionally crosslinked, for blowing the balloon, and adding an additional step to shrink the formed balloon. In one embodiment the pressure within the blown balloon is reduced to ambient and heated at a designated temperature while restraining the balloon longitudinally (axially). This causes the newly formed balloon to radially contract while the overall length of the shrunken balloon remains constant relative to its original formed length. This minimizes wall thickening as the balloon contracts. Without departing from the spirit of the invention, this additional step can be applied before or after the balloon is removed from the mold as an additional or separate operation in the balloon manufacturing sequence. Optionally, the axial restraint can involve increasing or decreasing the overall length of the shrunken balloon. Optionally, the pressure inside the balloon could be controlled at some level other than ambient.

FIG. 1 depicts a non-limiting embodiment of the present invention wherein step 0 refers to a polymer material that is first extruded or otherwise formed into a continuous tube of a desired length and outside and inside diameter and crosslinked by a suitable method. Step 1 refers to a continuous length of crosslinked polymer tube with wall thickness TwT and outer diameter ODT. A length of the tube (L1) is suitably utilized to form a balloon by heating (blow temperature) that portion of the tube (L1) in a mold, stretching (usually) and applying pressure (blow pressure) to the interior of the tube to expand the heated, stretched portion. Stretching before or while blowing the balloon results in axial orientation of the polymer in the balloon along with radial orientation (known in the art as biaxial orientation) and improves the balloon burst strength. As shown in FIG. 1, step 2, a tube with a "balloon" of outer diameter ODB, wall thickness TwB, and length L2, results. The outer diameter of the tube, ODT has remained unchanged and ODB is greater than ODT. The wall thickness of the balloon TwB is less than the wall thickness of tube TwT. As shown in step 2 of FIG. 1, it is preferred that the length of the blown balloon L2 be greater than L1.

The balloon is removed from the mold after cooling the mold and releasing the interior pressure. The portion of the tube containing the balloon is then reheated at or to a certain temperature (shrink temperature) while restraining the tube ends so that axial balloon contraction is restricted in a controlled manner. This controlled re-heating will cause the formed balloon to shrink, due to "memory", to some outer dimension ODS which will be less than the ODB of the unshrunk balloon, and whose length L3 is greater than L1. The exact shrunk balloon outer diameter ODS is determined by the length of time (shrink time) and shrink temperature that is applied to the balloon containing "memory". The higher the shrink temperature and the longer the shrink time, the greater the shrinkage, and the more closely the shrunken balloon diameter ODS will approximate the ODT of the tube from which it is being formed. By judicious application of combinations of shrink temperature and shrink time, the balloon may be shrunk to any size between the unshrunk balloon diameter ODB and the original diameter ODT of the tubing from which it was constructed. A wall thickness TwS of the shrunken balloon will be associated with a given shrunken balloon diameter ODS. The greater the shrinkage the greater the degree to which the wall thickness TwS will tend to increase relative to the unshrunk balloon wall thickness TwB. However the increase in wall thickness can be controlled by restraining the ends of the tube while the balloon is heated for the purpose of shrinking.

As noted above, while the shrink temperature and shrink time is being applied, the ends of the tube are suitably restrained by being subjected to one of the following restraining alternatives. The tube ends may be restrained so as to maintain the same original overall length that the tube exhibited with the formed balloon still in place (L3=L2) (shown). Alternatively, the tube ends may be longitudinally elongated while the shrink temperature and shrink time is being applied, preferably to a predetermined length, so that L3>L2. In a least preferred alternative, the balloon may be allowed to longitudinally contract in a controlled manner so that L3<L2>L1. However, this will result in a thickening of the shrunk balloon wall TwS to a greater extent than in the more preferred alternatives. In an extreme application of the least preferred alternative, L3 =L1 and the balloon would fully contract radially and axially resulting in the original tube being reformed similar to a piece of shrink tubing. Needless to say this is to be avoided for the purpose of a useful medical balloon. However for the formation of shrink tubing this would be an acceptable consequence.

In general terms, the application of a suitable combination of shrink temperature and shrink time in combination with the "memory" effect, results in the formation of an expandable portion within a tube. This expandable portion thereby contains a susceptibility to preferably expand upon introduction of pressure to the interior of the tube. The expandability is expressed in a compliance curve wherein the size of the expandable balloon portion varies with the amount of pressure introduced to the interior of the tube. This compliance curve can be a straight linear line or a non-straight non-linear line depending on the combination of the specific material employed, the shrink temperature and the shrink time applied, and the extent to which the balloon shrinks during the process. The tube now is an expandable element that contains an expandable portion (where the balloon was formed) and a less expandable portion (where no balloon was formed) and may be joined to a catheter to complete a medical dilatation device. A novel method to join a crosslinked expandable element to medical catheter is described below.

As shown in FIG. 1, step 3 an expandable portion of outer diameter ODS and wall thickness TWS is formed within a less expandable tube portion of outer diameter ODT and wall thickness TWT. The expandable portion has a length L3. This portion can be restrained so that L3 is equal to L2 (shown). Alternatively, the expandable portion can be longitudinally elongated so that L3 is greater than L2 (not shown). In either case, the wall thickness of the expandable portion TwS is less than the wall thickness of the tube (less expandable portion) TwT, since L3>L1. The outer diameter of the expandable portion ODS can be any value between ODB and ODT. In one embodiment, the outer diameter of the entire tube (the expandable and less expandable portions) is uniform and is equal to the outer diameter of the original tube ODT forming a dilation catheter of uniform outer diameter. This specific embodiment was the subject of co-pending application U.S. Ser. No. 09/558,355 titled "Dilation Device of Uniform Outer Diameter".

The balloon formation process may involve optional steps not mentioned above with out departing from the essence of the invention. For example optionally, the balloon could be free blown, that is without a mold. Optionally the tube may be axially stretched after the blow molding process. This results improved formation of the tapered ends of the balloon. Less preferentially L3 can be less than L2. After blow molding, the tube may be optionally heated at a higher temperature than the blow temperature to allow the balloon polymer to crystallize or anneal, prior to cooling the balloon and releasing the blow pressure to the balloon. Also, optionally the balloon may be shrunk while in the mold but with the interior pressure released during the application of shrink temperature and time. The shrink temperature/time profile can be in the form of a step curve, a linear or non-linear ramped curve, or any combination thereof.

As stated above, the dilatation device of the present invention is suitably fabricated from a polymer material, preferably a thermoplastic. A wide variety of polymers may be used in accordance with the present invention, including thermoplastic polymers and thermoplastic elastomer polymers such as polyamide elastomer polymers, polyester elastomer polymers, polystyrene elastomer polymers, thermoplastic polyurethane elastomer polymers, and blends of rubber and thermoplastic polymers. Thermoplastic elastomers suitable for this invention include the so-called thermoplastic elastomer block co-polymers such as polyamide elastomer block co-polymers which are sold under the trademarks PEBAX, VESTAMID, and GRILAMID by Atochem, Creanova, and American Grilon, respectively, and polyester elastomer block co-polymers such as HYTREL, LOMOD, ECDEL, PELPRENE, and ARNITEL, which are manufactured by DuPont, GE, Eastman, Toyobo and DSM, respectively. In addition, the styrenic block co-polymers such as SBS (styrenic polybutadienic), SIS (styrenic polyisoprenic) and S-EBS (styrenic polyethylene-butylenic) copolymers can be used. These are manufactured by Shell, Kuraray and others as KRATON and SEPTON, respectively. In addition, polyurethane block copolymers also known as thermoplastic polyurethanes may be used. Thermoplastic polyurethanes may comprise aliphatic or aromatic isocyanate groups in combination with aliphatic or aromatic polyester, polyether, polycarbonate, or polyurea groups. Suitable thermoplastic polyurethanes include polyester or polyether based aromatic polyurethanes such as PELLETHANE available from Dow Plastics, ESTANE available from BF Goodrich, TEXIN available from Bayer, and TECOTHANE available from Thermedics; polycarbonate based aromatic polyurethanes such as BIONATE available from The Polymer Technology Group (PTG), and CHRONOFLEX AR available from Cardiotech; polyether based aliphatic polyurethanes such as TECOPHILIC available from Thermedics, polycarbonate based aliphatic polyurethanes such as CARBOTHANE available from Thermedics; aromatic polyurethane polyether ureas such as BIOSPAN available from PTG; polycarbonate/polyether based aromatic polyurethanes such as CARBOSIL available from PTG; or aromatic or aliphatic polyurethanes with silicone/polyether soft segments such as PURSIL available from PTG or ELASTEON available from Aortech. Other suitable polyurethane block copolymers may be used including TECOPLAST available from Thermedics, and ISOPLAST available from Dow. Further, the following thermoplastic polymers may also be used in accordance with the present invention: PET (polyethylene terephthalate); PBT (polybutylene terephthalate); fluoropolymers such as PVDF (polyvinylidene difluoride) such as KYNAR, manufactured by Atochem; fluoroelastomers such as VITON manufactured by Dupont; PVC (polyvinyl chloride); various polyolefins such as polypropylene, polyethylene or the polyethylene co-polymers such as ENGAGE manufactured by Dow, or ethylene propylene co-polymers such as EPDM and EPR; polyamides such as NYLON 12 or NYLON 11 manufactured by Atochem and others, NYLON 6 or 6,6, and other aliphatic or aromatic polyamides; and blends of the above polymers. In addition blends of various rubbers with the above polymers may be used. The rubber is usually partially or fully crosslinked during the blending operation and the thermoplastic is uncrosslinked to form one subclass of type of a generic class of polymers termed "thermoplastic elastomers" termed a "TPO" or thermoplastic polyolefin elastomers. Common rubbers used for making blends with thermoplastics include EPDM, Butyl rubber, Natural rubber, Nitrile rubber, and EPR. These are usually blended with polypropylene, polyethylene, PVC, or chlorinated polyethylene, although other rubber/thermoplastic blends are known. In certain instances it might be possible to use elastomer materials or natural rubber in the present invention. Elastomers are synthetic thermosetting polymers with properties similar to vulcanized natural rubber. They exhibit the ability to be stretched to at least twice their original length and to retract very rapidly to approximately their original length when released. Examples of elastomers are neoprene, nitrile, butyl, EPDM, silicone, and polyurethane rubbers. It should be noted that a copolymer is any macromolecule that comprises two or more dissimilar monomers. In contrast a block copolymer contains two or more segments of dissimilar monomers linked together. In the case of a thermoplastic elastomer block copolymer, at least one of the blocks or segments generally exhibits a reinforcing property or "hard" characteristic, while at least on other block or segment generally exhibits an elastomeric property or "soft" characteristic. The properties of the thermoplastic elastomer block copolymer results from the incompatibility of the different blocks and the resulting phase separation that occurs. Depending on the proportion of soft and hard blocks, either the hard segments tend to aggregate into distinct regions within an amorphous matrix composed of the aggregated soft segments or the reverse occurs. The hard segments provide tensile strength characteristics while the soft segments provide elastomeric characteristics to the polymer. High strength combined with elastomeric properties is only achieved if there are at least two hard segments per block copolymer, that is, a soft segment sandwiched between two hard segments such as in the case of SBS or similar block copolymers. The elastomeric block copolymers can be distinguished from the TPO type thermoplastic polymers in that the TPO's are blends of two distinct polymers, a thermoplastic and an elastomer. In contrast, the elastomeric block copolymers contain elastomeric and thermoplastic characteristics within one polymer.

It should be understood that the materials discussed above are merely exemplary of polymers that may be used in accordance with the present invention; and a wide variety of materials can be used, including thermoset materials or castable materials or materials formed from solution, without departing from the spirit of the present invention as long as they possess or can be induced to possess "memory."

Polyamide/polyether block (PEBA) copolymers preferably have polyamide and polyether blocks or segments linked through ester linkages, i.e. polyamide/polyether polyesters. Polyamide/polyether polyester PEBA block copolymers are made by a molten state polycondensation reaction of a dicarboxylic polyamide and a polyether diol. The result is a short chain polyester made up of blocks or segments of polyamide and polyether. Such polymers are made up of at least two polyamide and at least two polyether segments. The polyamide and polyether blocks are not miscible. Thus, the materials are characterized by a two-phase structure having a thermoplastic region that is primarily polyamide and an elastomer region that is rich in polyether. The polyamide segments are semi-crystalline at room temperature. The generalized chemical formula for these polyamide/polyether polyester block copolymers may be represented by the following formula:

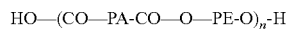

in which CO is a C=O moiety, PA is a polyamide hard segment, PE is a polyether soft segment, and the repeating number n is between 5 and 10. The polyamide hard segment is a polyamide of C6 or higher, preferably C10-C12, carboxylic acids; C6 or higher, preferably C10-C12, organic diamines; or C6 or higher, preferably C10-C12, aliphatic omega.-amino-alpha.-acids. The percentage by weight of the block copolymer attributable to the polyamide hard segments is between about 50% to about 95%. The polyether soft segment is a polyether of C2-C10 diols, preferably C4-C6 diols.

The polyamide segments are suitably aliphatic polyamides, such as nylons 12, 11, 9, 6, 6/12, 6/11, 6/9, or 6/6. Most preferably they are nylon 12 segments. The polyamide segments may also be based on aromatic polyamides but in such case significantly lower compliance characteristics are to be expected. The polyamide segments are relatively low molecular weight, generally within the range of 500-8,000, more preferably 2,000-6,000, most preferably about 3,000-5,000. Another range that is of interest is 300-15,000.

The polyether segments are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers that may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1,000. Another range that is of interest is 200-6,000.

The weight ratio of polyamide to polyether in the polyamide/polyether polyesters used in the invention desirably should be in the range of 50/50 to 95/5, preferably between 60/30 and 92/08, more preferably, between 70/30 and 90/10.

Polyamide/polyether polyesters are sold commercially under the PEBAX trademark by Atochem North America, Inc., Philadelphia, Pa. A suitable polymer grade for the intravascular balloon catheter of the invention is the PEBAX 33 series. In the embodiment in which the balloon is 100% PEBAX or a blend of PEBAX and a polyamide, preferably PEBAX and nylon, the presently preferred PEBAX polymers have a hardness of Shore D durometer of at least about 60D, preferably between about 60D to about 72D, i.e. PEBAX 6033 and 7233. In the embodiment in which the balloon is a co-extruded multi-layered balloon with at least one layer formed of PEBA, the presently preferred PEBAX polymers have a hardness of Shore D durometer of at least about 35 D, preferably between about 35D to about 72D, i.e. PEBAX 3533 and 7233.

The PEBAX 7033 and 6333 polymers are made up of nylon 12 segments and polytetramethylene ether segments in about 90/10 and about 80/20 weight ratios, respectively. The average molecular weight of the individual segments of nylon 12 is in the range of about 3,000-5,000 grams/mole and of the polytetramethylene ether segments are in ranges of about 750-1,250 for the 6333 polymer and about 500-800 for the 7033 polymer. The intrinsic viscosities of these polymers are in the range of 1.33 to 1.50 dl/g. Generally speaking, balloons of PEBAX 7033 type polymer exhibit borderline non-compliant to semi-compliant behavior and balloons of Pebax 6333 type polymer show semi-compliant to compliant distention behavior, depending on the balloon forming conditions.

While the PEBAX-type polyamide/polyether polyesters are most preferred, it is also possible to use other polyamide elastomer polymers with the physical properties specified herein and obtain similar compliance, strength and softness characteristics in the finished balloon. Such other polyamide elastomer polymers generally have polyamide segments and elastomer segments. The polyamide segments can be any aromatic or aliphatic polyamide and the elastomer segment can be any polyether, polyester or combination thereof.

The presently preferred PEBAX material has an elongation at failure at room temperature of at least about 150%, preferably about 300% or higher, and an ultimate tensile strength of at least 6,000 psi. The balloon has sufficient strength to withstand the inflation pressures needed to inflate the balloon and compress a stenosis in a patient's vessel. The burst pressure of the balloon is at least about 10 ATM, and is typically about 16-21 ATM. The wall strength of the balloon is at least about 15,000 psi (103 MPa), and typically from about 25,000 psi (172 Mpa) to about 35,000 psi (241 MPa).

As an alternative to polyamide elastomers, it is also possible to utilize polyester/polyether segmented or randomized block copolymers also known as polyester elastomer block copolymers, and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol. The generalized formula is

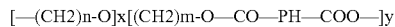
[—(CH2)n-O]x[(CH2)m-O—CO—PH—COO—]y

Where CO signifies a C=O moiety, COO signifies a carboxylic moiety, and PH signifies a phenyl moiety, and n can be between 2 and 10 and m can be 2 or 4.

Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids.

Polyester/polyether block copolymers are poly(butylene terephthalate)-block-poly(tetramethylene oxide) polymers such as Arnitel EM 740, sold by DSM Engineering Plastics or Hytrel polymers, sold by DuPont.

Thermoplastic polyurethanes are block copolymers that are the reaction product of a diisocyante a short chain diol chain extender and a polyahl. The diisocyanate useful as a reactant in forming the polyurethanes employed in the present invention can be selected from commercially-available aliphatic or aromatic isocyanates such as, for example, 1,6-hexamethylene diisocyanate ("HDI"), isophorone diisocyanate ("IPDI"), ethylene diisocyanate, 1,4-tetramethylene diisocyanate, 2,2,4-trimethyl-1,6-hexamethylene diisocyanate, 1,10-decanemethylene diisocyanate, 1,12-dodecanemethylene diisocyanate, cyclohexane-1,3 diisocyanate, cyclohexane-1,4-diisocyanate, 1-isocyanato-2-isocyanatomethyl cyclopentane, isophorone diisocyanate, bis-(4-isocyanatocyclohexyl)-methane, 1,3- and/or 1,4-bis(isocyanatomethyl)-cyclohexane, bis-(4-isocyanato-3-methyl-cyclohexyl)-methane, 1-isocyanato-1-methyl-4(3)-isocyanatomethyl cyclohexane, 4,4'-dicyclohexylmethane diisocyanate ("H12MDI"), methylene bis-(phenylisocyanate) ("MDI") an 80/20 mix of 2,4-tolylene diisocyanate (80% wt.) and 2,6-tolylene diisocyanate (20% wt.) ("TDI")", and combinations thereof.

The "polyahl" useful as a reactant in forming the polyurethanes employed in the present invention is an active hydrogen-containing compound that is reactive with the aliphatic polyisocyanate to produce the desired polyurethane. In addition, the term polyahl is intended to encompass compounds that react to generate an active hydrogen-containing moiety such as imines. An active hydrogen group is a group which has a hydrogen atom which, because of its position in the molecule, displays activity according to the Zerewitnoff test described by Woller in the Journal of American Chemical Society, Vol. 49, page 3181 (1927). Illustrative of such active hydrogen groups are —OH, —NH— —COOH, —SH and —CONH—. Particularly suitably polyahls include polyols, imines (such as ketimines and aldimines), oxazolidines, and combinations thereof, preferably having a weight average molecular weight of between about 100 and about 10,000, more preferably between about 100 and about 5,000, most preferably between about 200 and about 2,000.

Suitable amines are aliphatic or cycloaliphatic, primary or secondary amines. Preferred amines are poly(alkyleneoxy) alkylamines.

Suitable polyols include polyether polyols and polyester polyols. The preferred polyols useful in the present invention have a hydroxyl functionality of no greater than about 2, more preferably less than 1.5, advantageously about 1. The polyether polyols are prepared by polymerization of alkylene oxides with water, polyhydric alcohols with two to eight hydroxyl groups, or amines. Polyester polyols are suitably prepared by a condensation reaction of a polycarboxylic acid with a polyhydric alcohol. Some commercially available polyols include polybutadiene glycol ("PBDG"), poly(1,2-oxypropylene) glycol ("PPG"), poly(oxytetramethylene)glycol ("PTMEG"), poly(hexamethylene carbonate) glycol ("PHC"), poly(e-caprolactone) glycol ("PCL"), and poly(tetramethyelene adipate) glycol ("PTAd").

Some commercial short chain diol chain extenders include 1,4 butanediol, 1,4-cyclohexanedimethanol, 1,4-bis(2-hydroxyethoxy)benzene, 4,4'-methylene-bis(2-chloroaniline), and trimethylene gylcol di (p-aminobenzoate).

In preparing the polyurethanes useful in the present invention, the ratio of NCO equivalents in the polyisocyanate to the OH equivalents in the active hydrogen-containing compound is balanced to yield a linear macromolecule.

Catalysts are typically employed in the polyurethane-forming reaction. Useful catalysts include those that facilitate the reaction of the polyahl with the aliphatic polyisocyanate reactants. Suitable catalysts are the organotin catalysts, alone or in combination with amine catalysts, particularly tertiary amine catalysts. Illustrative organotin catalysts include dibutyltin dilaurate, stannous octoate, and combinations thereof. Illustrative amine catalysts include the following: N,N'-dimethylethanolamine, N,N-dimethylamino-ethoxyethanol, N,N'-dimethylaminoethyl-N-methylethanolamine, N,N-dimethyl-N',N'-2-hydroxypropyl-1,3-propylene diamine, N,N,N'-trimethyl-N'-hydroxyethyl-bis(amino ethyl) ether, N,N-bis(3-dimethylaminopropyl) amino-2-propanol, and combinations thereof. The catalysts are suitably employed in the polyurethane-forming formulation in a total amount of between about 0.01% and about 5%, preferably between about 0.01% and about 1%, by weight based upon the weight of the polyurethane-forming composition.

In preparing the desired polyurethane, the polyether polyol(s), polyisocyanate(s), chain extender(s) such as polyether or polyester glycol chain extenders, and other desired components are reacted, typically at an elevated temperature. An alternative method involves batch processing, followed by grinding and extrusion of the formed elastomer as is well-known in the art. Two basic commercial methods are utilized for polyurethane polymerization. Either the pre-polymer method (2 step) or the one-shot (1 step) method although the one-shot method seems to be preferred by industry. The one-shot process, or the pre-polymer process may be carried out using either bulk polymerization or solution polymerization. In the pre-polymer method, step 1 is where the diisocyanate reacts with the polyahl to form a relatively low molecular weight pre-polymer. Then in step 2 the pre-polymer reacts with the chain extender to form the high molecular weight polyurethane elastomer. That is, in the pre-polymer process, all or a portion of one or more of the isocyanate reactive materials is reacted with a stoichiometric excess of the polyisocyanate to form an isocyanate-terminated pre-polymer. This pre-polymer is then allowed to react with the remaining isocyanate-reactive materials to prepare the polyurethane and/or polyurea elastomer. The pre-polymer can be prepared with either the polyether or the chain extender, or a mixture of both.

In the one shot method all the polyurethane components are mixed together in the proper stoichiometric balance at one time, that is, all the isocyanate-reactive components are reacted simultaneously with the polyisocyanate. In such process, it is normal practice to blend all components except the polyisocyanate into a "B-side" mixture, which is then reacted with the polyisocyanate to form the polyurethane and/or polyurea elastomer. However, the order of mixing is not critical as long as the components do not undesirably react before all components are present. The reaction mixture is then suitably placed in a mold, or extruded through continuous processing utilizing an extruder, as illustrated by the disclosures of U.S. Pat. No. 3,642,964, incorporated herein by reference in its entirety, and cured at a suitable temperature. The apparatus used for blending and molding is not especially critical. Hand mixing, conventional machine mixing, and the so-called reaction injection molding (RIM) equipment are all suitable. The polymerization proceeds to completion yielding a high molecular weight thermoplastic polyurethane elastomer with alternating hard and soft segments. The one-shot method is intended to also include the process whereby the diisocyanate has been converted to a quasi pre-polymer by reaction with a minor amount (i.e., less than about 10 percent on an equivalent basis) of polyol prior to carrying out the polyurethane forming reaction.

In preparing the desired polyurethane, urethane-forming catalysts can be used, as discussed above, as well as the usual compounding ingredients such as antioxidants or other anti-degradents. Typical antioxidants include hindered phenols, butylated hydroxytoluene ("BHT"), and the like. Other optional compounding ingredients include, for example, plasticizers, adhesion promoters, fillers and pigments like clay, silica, fumed silica, carbon black, talc, phthalocyanine blue or green, TiO2, U-V absorbers, MgCO3, CaCO3 and the like. The compounding ingredients are suitably employed in an amount of between 0 and about 75 weight percent based upon the weight of the elastomer. When solution polymerization is used, polar solvents such as tetrahydrofuran ("THF"), dimethylformamide ("DMF"), and dimethylacetamide ("DMAC") are typically utilized.

The mixing of the reactants can be carried out at ambient temperature (typically from 20 deg C. to 25 deg C.) and the resulting mixture is then heated to a temperature of the order of about 40 deg C. to about 130 deg C., preferably to a temperature of about 90 deg C. to about 120 deg C. Alternatively, and preferably, one or more of the reactants is preheated to a temperature within the above ranges before the admixing is carried out. Advantageously, in a batch procedure, the heated reaction components are subjected to degassing in order to remove entrained bubbles of air, water, or other gases before the reaction takes place. This degassing is accomplished conveniently by reducing the pressure under which the components are maintained until no further evolution of bubbles occurs. The degassed reaction components are then admixed and transferred to suitable molds or extrusion equipment or the like and cured at a temperature of the order of about 20 deg C. to about 115 deg C. The time required for curing will vary the temperature of curing and also with the nature of the particular composition, as is known in the art.

As stated previously, a wide variety of polymers may be used in accordance with the present invention, as long as the materials either possess or are capable of being induced with "shape memory". With respect to thermoplastic polymers, memory may be imparted to polymers or blends of polymers less preferably through mechanical means, for example by stretching or more preferably by chemical means, for example by crosslinking.

Crosslinking results from the application of energy to the polymer alone or sometimes as a composition that includes the presence of one or more functional materials. At times the polymer itself is "functionalized" by grafting or otherwise incorporating a functional group within the chemical structure of the polymer. Suitable energy sources include thermal energy; radiated energy, such as visible light, infrared radiation, ultraviolet ("uv") light, gamma and x-rays, microwaves and radio frequency radiation; and particle beams such as neutron beams, proton beams or beta rays (also known as electron beam radiation); or combinations thereof. The energy source should be of sufficient magnitude so as to be capable of ionizing or generating free radicals or otherwise interacting with the polymer so as to impart crosslinks between polymer chains. Crosslinks are typically covalent or other chemical bonds between adjacent or nearby polymer chains. The energy output from the energy source required to crosslink the thermoplastic composition can vary over a wide range. For example when using e-beam irradiation, an amount of radiation of from about 1 and about 100 MegaRads, or between 2 and 20 MegaRads, or between 10 and 15 MegaRads, or typically 12.5 MegaRads may be imparted to a composition to crosslink the composition. The exact dose being determined by the properties desired in combination with the crosslinkability of the polymeric material employed. In addition the dose must be applied over a suitable period of time to insure that the polymer composition being irradiated does not overheat. The energy source may interact with the polymer and/or the functional material to form ions, free radicals or other chemically reactive species that then combine in a suitable manner to yield a crosslinked polymer.

The application of energy to the polymer must be controlled to maximize crosslinking and minimize degradation of the polymer or the formation of unwanted by-products. This is often accomplished by addition of a co-agent to a polymer prior to applying energy for the purpose of crosslinking. The co-agent often functions by decreasing the amount of energy required to crosslink a given polymer, thereby favoring the occurrance of crosslinking rather than chain scission as the predominant chemical reaction. Polymer degradation is usually manifest by chain scission, lowering of molecular weight and decrease in tensile strength or increase in elongation. Polymer crosslinking usually is manifest by an increase in molecular weight, increase in tensile strength, and a decrease in elongation. Furthermore a crosslinked polymer usually no longer melts nor dissolves in typical solvents.

Suitable functional materials include peroxidic compounds, photosensitizers, and coagents of functionality greater than 2 also known as crosslinkers, crosslinking agents or reactive monomers, oligomers and polymers. Without going into detail about the various mechanisms by which crosslinking occurs, it may be broadly stated that functional materials serve to initiate the crosslinking reaction or increase its efficiency. In addition, some materials serve as strictly as catalysts, while others are ultimately incorporated in part or as a whole within the crosslink or otherwise become part of the polymer structure.

Peroxidic organic compounds, may be defined as an organic compound that possesses at least one oxygen-oxygen bond. Photosensitizers are compounds and compositions that become reactive upon exposure to light in the UV or visible spectrum. Co-agents are most often ethylenically unsaturated monomers, oligomers, polymers or chemical groups having a functionality of two or greater. Although co-agents of higher unsaturation such as diacetylenes are known they are rarely used. Co-agents may be used alone or in combination with peroxidic compounds or photoinitiators to decrease the energy required to effect the crosslink, or impart some desired property to the polymer. Co-agents or "crosslinkers" function generally to link together polymer chains into a two or three dimension structure. Crosslinkers can be divided into at least two groups: "internal" and "external". Both external and internal crosslinkers can be used in the practice of this invention. Internal crosslinkers are monomers or oligomers that are structurally incorporated into the polymeric backbone of the polymers to be crosslinked. Internal crosslinkers may be existing functionalities in the polymer (such as double bonds in unsaturated polyolefins), or may be functionalities added specifically for the purpose of creating crosslinking capability. External crosslinkers, by comparison, are induced to link already substantially polymerized polymers, and are mixed together with the polymers to be crosslinked. Preferrable external crosslinkers include multifunctional monomers, oligomers or polymers.

Examples of functional materials are:

a) Typical peroxidic organic compounds include peroxides and hydroperoxides such as tert-butyl hydroperoxide, cumene hydroperoxide, diisopropylbenzene hydroperoxide, 2,5-dimethylhexane-2,5-dihydroperoxide, p-menthane hydroperoxide; 1,1,3,3-tetramethylbutyl hydroperoxide, acetyl peroxide, benzoyl peroxide, p-chlorobenzoyl peroxide, 2,4-dichlorobenzoyl peroxide, ditoluoyl peroxide, decanoyl peroxide, lauroyl peroxide, isobutyryl peroxide, diisononanoyl peroxide, pelargonyl peroxide, tert-butyl peroxyacetate, tert-butyl peroxymaleic acid, tert-butyl peroxyisobutyrate, tert-butyl peroxypivalate, tert-butyl peroxybenzoate, tert-butyl peroxycrotonate, tert-butyl-Peroxy-(2-ethylhexanoate), 2,5-dimethyl-2,5-bis-(2-ethylhexanoylperoxy) hexane, 2,6-dimethyl-2,5-bis-(benzoylperoxy) hexane, 2,5-dimethyl-2,5-bis-(tert-butylperoxy) hexane, 2,5-dimethyl-2,5-bis-(tert-butylperoxy)-hexyne-3, di-tert-butyl diperoxyphthalate, 1,1,3,3-tetramethylbutylperoxy-2-ethyl-hexanoate, di-tert-butyl peroxide, di-tert-amyl peroxide, tert-amyl-tert-butyl peroxide, 1,1-di-tert-butylperoxy-3,3,5-trimethyl cyclohexane, bis-(tert-butylperoxy)-diisopropylbenzene, n-butyl-4,4-bis-(tert-butylperoxy)valerate, dicumyl peroxide, acetyl acetone peroxide, methyl ethyl ketone peroxide, cyclo hexanone peroxide, tert-butylperoxy isopropyl carbonate, 2,2-bis-(tert-butylperoxy) butane, di-(2-ethylhexyl) peroxydicarbonate, and bis-(4-tert-butylcyclohexyl)peroxydicarbonate.

b) Typical of the photosensitizers are aliphatic and aromatic ketones, for example: acetophenone, acetoin, 1'-aceto naphthone, 2'-acetonaphtone, anisoin, anthrone, bianthrone, benzil, benzoin, benzoin methyl ether, benzoin isopropyl ether, 1-decalone, 2-decalone, benzophenone, p-chlorobenzophenone, dibenzalacetone, benzoylacetone, benzylacetone, deoxyanisoin, deoxybenzoin, 2,4-dimethylbenzophenone, 2,5-dimethylbenzophenone, 3,4-dimethylbenzophenone, 4-benzoylbiphenyl, butyrophenone, 9-fluorenone, 4,4-bis(dimethylamino)-benzophenone, 4-dimethylaminobenzophenone, dibenzyl ketone, 4-methylbenzophenone, propiophenone, benzanthrone, 1-tetralone, 2-tetralone, valerophenone, 4-nitrobenzophenone, di-n-hexyl ketone, isophorone, and xanthone. Aromatic ketones are preferred. Particularly preferred are benzophenone, benzoin, anthrone and deoxyanisoin. Also useful as photosensitizers are quinones, for example: anthraquinone, 1-aminoanthraquinone, 2-aminoanthraquinone, 1-chloroanthraquinone, 2-chloroanthraquinone, 2-ethylanthraquinone, 1-methylanthraquinone, 2-methylanthraquinone, 1-nitroanthraquinone, 2-phenylanthraquinone, 1,2-napththoquinone, 1,4-naphthoquinone, 2-methyl-1,4-naphthoquinone, 1,2-benzanthraquinone, 2,3-benzanthraquinone, phenanthrenequinone, 1-methoxyanthraquinone, 1,5-dichloroanthraquinone, and 2,2'-dimethyl-1,1'-dianthraquinone, and anthraquinone dyes. Preferred quinones are 2-methyl anthraquinone, 2-chloroanthraquinone and 2-ethylanthraquinone. Still other compounds that can be used as the photosensitizer are azo compounds. Typical of the useful compounds are: 2-azo-bisisobutyronitrile, 2-azo-bispropionitrile, dimethyl-2-azo-bisisobutyrate, 1-azo-bis-1-cyclohexanecarbonitrile, 2-azo-bis-2-methylheptanitrile, 2-azo-bis-2-methylbutyronitrile, 4-azo-bis-4-cyanopentanoic acid, azodicarbonamide, azobenzene, and azo dyes. Other photosensitizers will be apparent to those skilled in the art. Among these are: aromatic hydrocarbons such as, naphthalene, anthracene, phenanthrene, and 1-phenyldecane; aromatic nitro compounds such as, nitrobenzene, pnitroanisole, 4-nitrobiphenyl, p-nitroaniline, and 2,4,6-trinitroaniline; aldehydes, for example, 2-ethylhexanal, tetradecyl aldehyde, phenylacetaldehyde, benzaldehyde, p-anisaldehyde, 4-benzyloxybenzaldehyde, 3,4-dibenzyloxybenzaldehyde, p-n-octyloxybenzaldehyde, Inaphthaldehyde, 2-naphthaldehyde, and 9-anthraldehyde; organic sulfur compounds, for example, diphenyl disulfide, dibenzyl disulfide, dibenzoyl disulfide, dilauroyl disulfide, 1-naphthalenethiol, diisopropylbenzene thiol, 2-mercaptobenzothiazole, 2-mercaptobenzimidazole, tetramethylthiuram monosulfide, tetramethyl thiuram disulfide, ethyl-2-benzothiazylsulfonate, and p-toluenesulfonyl chloride; organic halogen compounds such as chlorinated paraffins, chlorinated biphenyls and polyphenyls, chlorinated toluene, xylenes, etc., benzyl chloride, 3,4-dimethylbenzyl chloride, benzyhydryl chloride, benzal chloride, benzotrichloride, chlorinated naphthalenes, 1-chloromethylnaphthalene, tetrachloro-tetrahydronaphthalene, phenacyl chloride, phenacyl bromide, and styrene dibromide; aryl amines such as aniline, N,N-diethyl aniline, diphenylamine, triphenylamine, 1-naphthylamine, 2-naphthylamine, p,p'-benzylidenebis (N, Ndimethylaniline), p,p',p"-triaminotriphenylmethane, p,p',p"-triaminotriphenyl carbinol, and 4,4'-diaminobiphenyl. Combinations of two or more photosensitizers may also be used.

c) Typical examples of ethylenically unsaturated polyfunctional co-agents include (i) Divinyl compounds such as divinylbenzene. divinyl succinate, divinyl adipate, divinyl maleate, divinyl oxalate, divinyl malonate, (ii) Allyl compounds such as diallyl phthalate (DAP), diallyl isophthalate, diallyl adipate, diallyl glycolate, diallyl maleate, diallyl sebacate, triallyl phosphate, triallyl aconitate, allyl trimellitate and allyl pyromellitate; diallyl carbonate; diallyl succinate; diallyl tetrabromophthalate; diethyl diallylmalonate; dimethyl diallylmalonate; and 2,2,6,6-tetrabromobisphenol A diallyl ether. 2,5-diallyl-4,5dimethyl-2-cyclopenten-1-one; diallyl fumarate; diallyl itaconate; 1,3,5-triallyl-2methoxybenzene; triallyl trimesate; triallyl trimellitate; pentaerythritol triallyl ether; tetraallyl cis, cis, cis, cis-cyclopentane-1,2,3,4-tetra-carboxylate; N,N,N',N'-tetraallylethylenediamine. 1,3,5 triethyl benzene; 1,2,4 triethyl benzene; and 1,3,5 triisopropyl benzene diallyl phthalate and meta-phenylene dimaleimide; allyl methacrylate; diallyl maleate; diallyl itaconate; diallyl diglycolate; diallyl oxalate; diallyl azelate; diallyl malonate; diallyl glutarate; triallylisocyanurate; triallylcyanurate.

(iii) Acrylic or methacrylic compounds such as 1,6-hexanediol diacrylate (HDDA), 1,6-hexanediol dimethacrylate (HDDMA), neopentyl glycol diacrylate, neopentyl glycol dimethacrylate, ethylene glycol diacrylate (EGDA), ethylene glycol dimethacrylate (EGDMA), polyethylene glycol diacrylate (PEGA), polyethylene glycol dimethacrylate (PEGMA), polypropylene diacrylate, polypropylene glycol dimethacrylate, butylene glycol diacrylate, butylene glycol dimethacrylate, pentaerythritol diacrylate, 1,4-butanediol diacrylate, trimethylolpropane triacrylate, trimethylolpropane trimethacrylate, pentaerythritol triacrylate, dipentaerythritol hexaacrylate, tetramethylolmethane tetraacrylate and N,N,N',N'-tetrakis(.beta.-hydroxyethyl)ethylene-diamine acrylate. 1,6-hexane diol diacrylate (HDODA), 1,6-hexane diol dimethacrylate (HDODM), trimethylolpropane triacrylate (TMPTA), trimethylolpropane trimethacrylate (TMPTM), pentaerythritol tetracrylate (PTA), and pentaerythritol tetramethacrylate (PTM). Other useful acrylates and methacrylates include pentaerythritol triacrylate, dipentaerythritol monohydroxy penta/acrylate, 1,3-butylene glycol diacrylate, 1,4-butene diol diacrylate, 2,2-dimethyl propane 1,3-diacrylate (neopentyl glycol diacrylate), diethylene glycol diacrylate, 1,3-butylene glycol dimethacrylate, ethylene glycol dimethacrylate, diethylene glycol dimethacrylate, treithylene glycol dimethacrylate, tetraethylene glycol dimethacrylate, polyethylene glycol dimethacrylate, and ethoxylated bisphenol A dimethacrylate. ethylene glycol diacrylate, ethylene glycol dimethacrylate, diethylene glycol diacrylate, diethylene glycol dimethacrylate, 1,3- and 1,4-butane diol diacrylate, 1,3- and 1,4-butane diol dimethacrylate, tolylene-2,4-diisocyanate, 4,4'-methylene bis(phenyl isocyanate), glyceryl triacrylate, and pentaerythritol tetraacrylate. methyl methacrylate, ethyl acrylate, 2-ethylhexyl acrylate, chlorohexyl acrylate, styrene, 2-chlorostyrene, 2,4-dichlorostyrene, acraylic acid, acrylamide, acrylonitrile, t-butyl acrylate, methylacrylate, butyl acrylate, 2-(N-butylcarbamyl) ethyl methacrylate, 2-(N-ethylcarbamyl)ethyl methacrylate, 1,4-butylene dimethacrylate, or diacrylate, ethylene dimethacrylate, hexamethylene diacrylate or dimethacrylate hexamethylene diacrylate or dimethacrylate, glyceryl diacrylate or dimethacrylate, glyceryl triacrylate or trimethacrylate, pentaerythritol triacrylate or trimethacrylate, pentaerythritol tetraacrylate or tetramethacrylate, diallyl phthalate, dipentaerythritol pentaacrylate, neopentylglycol diacrylate, and 1,3,5-tri(2-methacryloyloxyethyl)-s-triazine. In order to protect the acrylates or methacrylates, antioxidants may be added.

The following acrylates are commercially available from The Sartomer Corporation, 502 Thomas Jones Way Exton, Pa. 19341. Included in the list are the chemical name followed by the Sartomer catalog number.

1,3-butylene glycol diacrylate-SR-212, 1,3-butylene glycol dimethacrylate-SR-297
1,4-butanediol diacrylate-SR-213
1,4-butanediol dimethacrylate-SR-214
1,6 hexanediol diacrylate-SR-238
1,6 hexanediol dimethacrylate-SR-239
1-hydroxy-cyclohexyl-phenyl-ketone-Esacure KS300
2(2-ethoxyethoxy) ethyl acrylate-SR-256
2-hydroxyethylethylene urea-SR-512
2-hydroxyethylethylene urea (with water)-SR-511
2-phenoxyethyl acrylate-SR-339
2-phenoxyethyl methacrylate-SR-340
acrylate functional monomer-PC-300
acrylated polyester oligomer-CN293
aliphatic allyl oligomer-CN9101
aliphatic diacrylate monomer-PC201
aliphatic dimethacrylate monomer-PC101
aliphatic urethane acrylate-CN2900
aliphatic urethane acrylate-CN9788
aliphatic urethane acrylate-CN9893
aliphatic urethane diacrylate oligomer with acrylate monomer diluent-CN959
alkoxylated aliphatic diacrylate-SR-9209
alkoxylated cyclohexane dimethanol diacrylate-CD-580
alkoxylated cyclohexane dimethanol diacrylate-CD-581
alkoxylated cyclohexane dimethanol diacrylate-CD-582
alkoxylated diacrylate-CD-802
alkoxylated hexanediol diacrylate-CD-560
alkoxylated hexanediol diacrylate-CD-561
alkoxylated hexanediol diacrylate-CD-564
alkoxylated lauryl acrylate-CD9075
alkoxylated neopentyl glycol diacrylate-CD9043
alkoxylated nonylphenol acrylate-SR614
alkoxylated phenol acrylate-CD9087
alkoxylated tetrahydrofurfuryl acrylate-CD-611
alkoxylated trifunctional acrylate ester-SR-9008
allyl methacrylate-SR-201
amine modified polyether acrylate oligomer-CN-501
amine modified polyether acrylate oligomer-CN-550
amine modified polyether acrylate oligomer-CN-551
amine-modified epoxy acrylate-CN2100
aromatic urethane acrylate-CN2901
benzil dimethyl ketal-Esacure KB1
benzophenone-BP
caprolactone acrylate-SR-495
chlorinated polyester acrylate oligomer-CN2201
dibutoxyethoxyethyl formal-SR-660
cycloaliphatic diepoxide-SarCat® K126
cyclohexane dimethanol diacrylate-CD-406
cyclohexane dimethanol dimethacrylate-CD-401
diethylene glycol diacrylate-SR-230
diethylene glycol dimethacrylate-SR-231
dipentaerythritol pentaacrylate-SR-399
dipropylene glycol diacrylate-SR-508
di-trimethylolpropane tetraacrylate-SR-355
epoxidized soybean oil acrylate-CN-111
epoxy acrylate-CN-104
epoxy methacrylate-CN-151
epoxy novolak acrylate blended with sr-351-CN-112C60
ethoxylated (10) bisphenol a diacrylate-SR-602
ethoxylated (10) hydroxyethyl methacrylate-CD-572
ethoxylated (15) trimethylolpropane triacrylate-CD-9035
ethoxylated (2) bisphenol a dimethacrylate-SR-348
ethoxylated (2) hydroxyethyl methacrylate-CD-570
ethoxylated (3) bisphenol a diacrylate-SR-349
ethoxylated (3) trimethylolpropane triacrylate-SR-454
ethoxylated (3) trimethylolpropane triacrylate-SR-454HP
ethoxylated (30) bisphenol a diacrylate-CD-9038
ethoxylated (30) bisphenol a dimethacrylate-SR-9036
ethoxylated (4) bisphenol a diacrylate-SR-601
ethoxylated (4) bisphenol a dimethacrylate-CD-540
ethoxylated (4) nonyl phenol acrylate-SR-504
ethoxylated (4) nonyl phenol methacrylate-CD-612
ethoxylated (4) pentaerythritol tetraacrylate-SR-494
ethoxylated (5) hydroxyethyl methacrylate-CD-571 ethoxylated (6) trimethylolpropane triacrylate-SR-499
ethoxylated (8) bisphenol a dimethacrylate-CD-542
ethoxylated (9) trimethylolpropane triacrylate-SR-502
ethoxylated(10) bisphenol dimethacrylate-SR-480
ethoxylated(20) trimethylolpropane triacrylate-SR-415
ethoxylated(6) bisphenol a dimethacrylate-SR541
ethyl 4-(dimethylamino) benzoate-Esacure EDB
ethylene glycol dimethacrylate-SR-206
glycidyl methacrylate-SR-379
isobornyl acrylate-SR-506
isobornyl methacrylate-SR-423
isodecyl acrylate-SR-395
isodecyl methacrylate-SR-242
isooctyl acrylate-SR-440
isopropyl thioxanthone-Esacure ITX
lauryl acrylate-SR-335
lauryl methacrylate-SR-313
metallic diacrylate-SR-636
metallic diacrylate-SR-638
metallic diacrylate-SR-705
metallic diacrylate-SR-9016
metallic dimethacrylate-SR-708
metallic monomethacrylate-SR-709
methacrylate functional monomer-PC-301
methacrylate functional monomer-PC304
methoxy polyethylene glycol (350) monomethacrylate-CD-550
methoxy polyethylene glycol (550) monomethacrylate-CD-552
neopentyl glycol diacrylate-SR-247
neopentyl glycol dimethacrylate-SR-248
octyldecyl acrylate-CD-484
oligo (2-hydroxy-2 methyl-1-4 (1-methylvinyl) phenyl propanone (emulsion)-Esacure KIP/EM
oligo (2-hydroxy-2-methyl-1-4 (1-methylvinyl) phenyl propanone and 2-hydroxy-2-methyl-1-phenyl-1-propanone (monomeric)-Esacure KIP100F
oligo (2-hydroxy-2-methyl-1-4 (1-methylvinyl) phenyl propanone and 2-hydroxy-2-methyl-1-phenyl-1-propanone (polymeric)-Esacure KIP150
pentaacrylate ester-SR-9041
pentaerythritol tetraacrylate-SR-295
pentaerythritol triacrylate-SR-444
polybutadiene dimethacrylate-CN-301
polybutadiene dimethacrylate-CN-303
polybutadiene urethane diacrylate-CN-302
polyester acrylate-CN-292
polyester acrylate oligomer-CN2200
polyester acrylate oligomer-CN2250
polyester acrylate oligomer-CN2251
polyester acrylate oligomer-CN2252
polyester acrylate oligomer-CN2253
polyester acrylate oligomer-CN2254
polyethylene glycol (200) diacrylate-SR-259
polyethylene glycol (400) diacrylate-SR-344
polyethylene glycol (400) dimethacrylate-SR-603
polyethylene glycol (600) diacrylate-SR-610
polyethylene glycol (600) dimethacrylate-SR-252
polyethylene glycol dimethacrylate-SR-210
polypropylene glycol monomethacrylate-SR-604
propoxylated (2) allyl methacrylate-CD-513
propoxylated (2) neopentyl glycol diacrylate-SR-9003
propoxylated (3) glyceryl triacrylate-SR-9020
propoxylated (3) glyceryl triacrylate-SR-9020HP
propoxylated (3) trimethylolpropane triacrylate-SR-492
propoxylated (6) trimethylolpropane triacrylate-CD-501
siliconized urethane acrylate oligomer-CN-990
stearyl acrylate-SR-257
stearyl methacrylate-SR-324
tetraethylene glycol diacrylate-SR-268
tetraethylene glycol dimethacrylate-SR-209
tetrahydrofurfuryl acrylate-SR-285
tetrahydrofurfuryl methacrylate-SR-203
triaryl sulfonium hexafluorophosphate (50% in propylene carbonate)-SarCat® K185
tridecyl acrylate-SR489D
tridecyl methacrylate-SR493D
triethylene glycol diacrylate-SR-272
triethylene glycol dimethacrylate-SR-205
triethylene gylcol diacetate-SR-322
trifunctional acid ester-CD-9051
trifunctional acid ester-CD-9052
trifunctional acrylate ester-SR-9012
trifunctional methacrylate ester-SR-9009
trifunctional methacrylate ester-SR-9011
trifunctional urethane acrylate-CN-929
trifunctional urethane acrylate blended with sr-238-CN-945B85
trifunctional urethane acrylate blended with sr-306-CN-945A60
trimethylbenzophenone and methylbenzophenone-Esacure TZT
trimethylolpropane triacrylate-SR-351
trimethylolpropane triacrylate-SR-351HP
trimethylolpropane trimethacrylate-SR-350
tripropylene glycol diacrylate-SR-306
tripropylene glycol diacrylate-SR-306HP
tris(2-hydroxy ethyl)isocyanurate triacrylate-SR-368
tris(2-hydroxy ethyl)isocyanurate triacrylate-SR-368D
urethane acrylate-CN-962
urethane methacrylate-CN-1963
dibutoxyethoxyethyl adipate-SR-650

(iv) Allyl-acrylic compounds such as allyl acrylate and allyl methacrylate, and tris (2-hydroxy ethyl) isocyanurate triacrylate (v) Acrylamide and miscellaneous compounds such as N,N'-methylenebisacrylamide and N,N'-methylene-bis-methacrylamide. N,N'-methylene bis acrylamide, dimethallyl maleate, dimethallyl oxalate, dimethallyl malonate, dimethallyl succinate, dimethallyl glutarate, dimethallyl adipate, diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, butane diol dimethallyl ether, 3,3'-ethylidene bis(N-vinyl-2-pyrrolidone), 1,3-diallyl urea.

(vi) Oligomers having at least two ethylenically unsaturated groups such as polyurethane acrylate, epoxy acrylate, polyether acrylate and polyester acrylate, acrylated alkyls, acrylated epoxies, acrylated polyesters, acrylated polyacrylates such as the reaction product of acrylic acid with the copolymer methyl methacrylate and glycidyl acrylate, acrylated urethane and acrylated cellulose oligomers and polybutadiene and the like resins.

These crosslinking agents may be used singly or in the form of a mixture of two or more of them. Furthermore a solid or a highly viscous crosslinking agent may be used in the state of being dissolved in another liquid crosslinking agent or occassionally in a monofunctional monomer. For example, triallyl cyanurate or diallyl phthalate, which are ordinarily solid crosslinking agents at room temperature, may be dissolved in TMPTMA that is ordinarily a liquid at room temperature.

Examples of monofunctional monomers suitable to dissolve or reduce the viscosity of a polyfunctional acrylate are, acrylic acid (AAc), methacrylic acid (MAAc), methyl acrylate (MA), methyl methacrylate (MMA), ethyl acrylate (EA), ethyl methacrylate (EMA), butyl acrylate (BA), butyl methacrylate (BMA), hexyl acrylate, 2-ethylhexyl acrylate, 2-ethylhexyl methacrylate, isooctyl acrylate, lauryl methacrylate, 2-hydroxyethyl acrylate (HEA), 2-hydroxyethyl methacrylate (HEMA), 2-hydroxypropyl acrylate, 2-hydroxypropyl methacrylate, 3-chloro-2-hydroxypropyl methacrylate, N,N'-dimethylaminoethyl acrylate, N,N'-dimethylamino ethyl methacrylate, N,N'-diethylaminoethyl acryl ate, N,N'-diethylaminoethyl methacrylate, glycidyl acrylate (GA), glycidyl methacrylate (GMA), carbitol acrylate, tetrahydrofurfuryl acrylate, tetrahydrofurfuryl methacrylate, dicyclopentadienyl acrylate, dihydrodicyclopentadienyl methacrylate, isobonyl acrylate, acrylamide (AAm), methacrylamide (MAm), N-methlolacrylamide (N-MAM), N-diacetone-acrylamide (DAAM), Nvinylpyrrolidone, maleic acid, itaconic acid, styrene (ST), acrylonitrile (AN), vinyl acetate (VAc) and vinyltoluene (VT), though monomers that can be used are not limited to those exemplified above.

Especially preferable external crosslinkers include di- or tri-functional monomers. Most preferable crosslinkers include ethylene glycol dimethacrylate, triallyl isocyanurate (available as PERKALINK® 301 from Akzo Nobel), triallyl cyanurate (available as PERKALINK®300 from Akzo Nobel), or triallyl 1,3,5-triazine-2,4,6(1H,3H,5H)-trione (available from SAF, Inc.) and trimethylpropanoltrimethacrylate (available as SR-350 from Sartomer).

It has been found that the technical crosslinking agents, such as trimethylolpropane trismethacrylate or pentaerythritol tetraacrylate, or triallyisocyanurate contain as impurities small amounts of compounds that have not been completely esterified, for example trimethylolpropane bis-methacrylate and pentaerythritol tris-acrylate or diallylisocyanurate. Nevertheless, technical mixtures such as these may also be used in accordance with the invention provided they contain predominant quantities of completely esterified polyacrylates. However with respect to crosslinking of thermoplastic polyurethanes, it is preferable that the crosslinking agents be free of unesterified hydroxyl groups to avoid interactions with free isocyanate groups in the polymer. Therefore, it may be necessary to purify certain technical crosslinking agents to remove partially reacted co-agent moieties which contain unesterified hydroxyl groups when employed with certain polymers such as thermoplastic polyurethanes. This would be especially the case when the crosslinking agent is utilized with thermoplastic polyurethanes at high concentration exceeding 2 or 3%.

Functional materials may be added to polymers in liquid or solid form after they are polymerized, by compounding in single or twin screw extruders, by soaking the polymer in the material so it is absorbed into the polymer, or by swelling the polymer with a solvent in the presence of the functional material and then removing the solvent. They also may be added at the time of polymerization of the polymer provided they do not interfere with the polymerization reaction. If it is intended that the functional material be incorporated into the structure of the polymer they may be added at the time of polymerization or grafted on to the polymer backbone or reacted with a suitable polymer end group during or after polymerization.

It has been found particularly with respect to polyamide and polyamide elastomer type polymers such as PEBAX® or RILSAN® A (Nylon 12) or RILSAN B® (Nylon 11), that the addition of certain co-agents may result in the formation of an undesirable amount of gels. Gels are thought to be small regions of prematurely crosslinked or otherwise degraded polymer which result from exposure of the polymer to multiple heat processing cycles. Gels are particularly undesirable with respect to balloon catheters, since they form areas of stress concentration or other defects that weaken the wall of the balloon that may cause a premature failure of the balloon by lowering the burst pressure of the balloon. In order to minimize the formation of gels in these materials it was found beneficial to first prepare a concentrate of co-agent in PEBAX or RILSAN and then mix or blend the concentrate with the polymer. The ratio of the amount of unmodified polymer relative to the polymer with high amounts of co-agent is called the let down ratio. Since only the concentrate is exposed to multiple heat cycles, this procedure minimizes the amount of polymer exposed to an extra heat history and hence minimizes the formation of gels. Co-agent concentrations of 10-15% by weight were found possible by using a twin screw compounding extruder which allowed let down ratios for RILSAN or PEBAX of about 10:1 to 15:1, yielding a final additive level within the PEBAX OR RILSAN OF 1.5%.

Figure 1A:
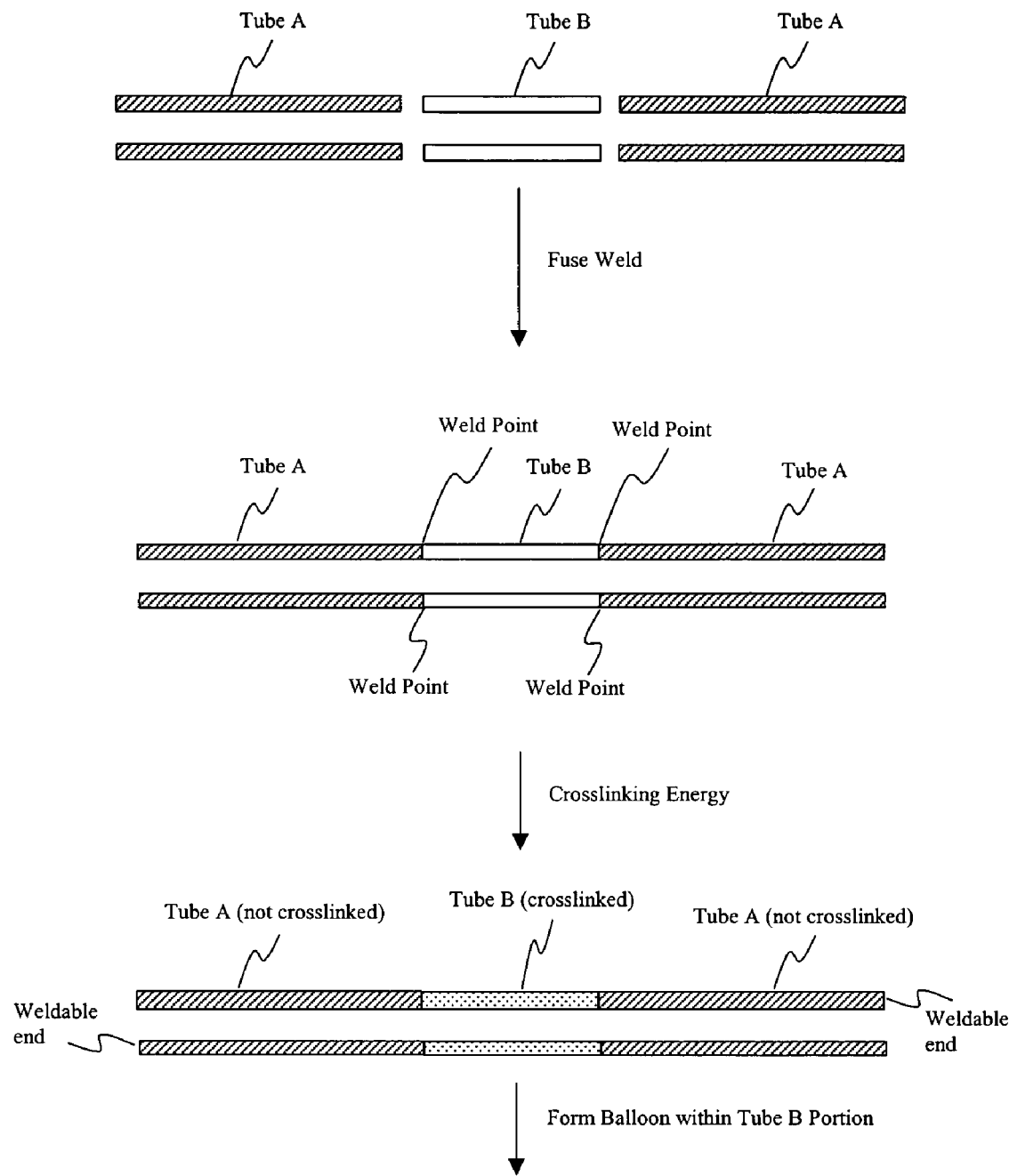
FIG. 1A is a drawing of the steps involved in forming a crosslinked balloon with weldable ends.
Figure 1C:
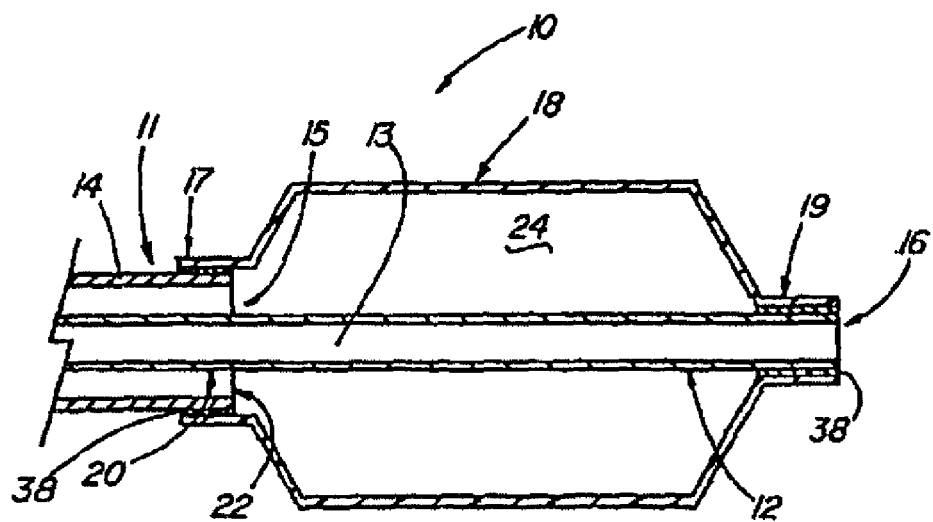
FIG. 1C is a drawing of the cross-section of the distal end of dilation catheter assembly showing a dilation balloon element.

In the construction of balloon catheters, once the balloon element is formed it is necessary to attach it in some manner to the remainder of the catheter assembly. As shown in FIG. 1C, the catheter assembly at the distal end of the catheter, 10, generally consists of a larger outer shaft, 11, constructed at least in part from a polymer tube, and a smaller inner shaft, 20, constructed at least in part from a polymer tube, located within the lumen of the outer shaft, 22, plus a tip (not shown). The proximal end, 17, of the balloon element, 18, is attached to the surface of the outer shaft, 14, and the distal end of the balloon, 19, is attached to the surface, 12, of the distal end of the inner shaft, 16. It should be noted that lumen, 13, of inner shaft 20, is utilized to contain the guide wire of the balloon catheter, and lumen, 22, of the outer shaft, 11, communicates with the lumen, 24, of the balloon element 18, at annulus, 15, and serves to supply the pressurizing fluid which pressurizes and expands balloon, 18. The preferred method of attachment is to weld the balloon element at the interface, 38, of the respective catheter shafts by applying heat and pressure. Welding provides smooth, flexible and strong joints between the component parts. Since the balloon element and the shafts are usually constructed at least in part from thermoplastic polymeric materials, the application of heat and pressure melts the thermoplastic polymeric materials and causes them to bond to each other. In the instance where a balloon element is composed of a crosslinked polymer, the welding cannot be performed since a crosslinked polymer is a thermoset, and no longer melts and usually will not bond to the shafts. One may then utilize a less preferred method that involves the use of adhesives to glue the balloon element to the catheter shafts at their respective interfaces, 38. The method is less preferred because it results in an undesirable thickening and stiffening of the catheter shaft at the point, 38 where the balloon element is joined to the catheter shafts. It would therefore be desirable if a means of welding a crosslinked balloon element to a catheter assembly were available. This can be accomplished if a component of the crosslinked balloon element is thermoplastic, and can therefore melt upon the application of heat energy. One embodiment of this concept for welding a crosslinked balloon to a catheter shaft would be to weld or otherwise attach lengths of a compatible and uncrosslinkable polymer tubing to one or both ends of a length of crosslinkable polymer tubing prior to exposure of the tubing assembly to crosslinking energy. The result would be a length of tubing consisting of a crosslinkable section with a non-crosslinkable section or sections at one or both outer ends. Upon exposure to crosslinking energy, only the crosslinkable portion will crosslink, while the outer end or ends will remain uncrosslinked. Thus, after applying crosslinking energy, a tubing assembly will be obtained with a crosslinked area and a non-crosslinked area. The non-crosslinked area would be located at one or both ends of the tubing assembly and would be weldable. In the case where the crosslinked section of tubing is centrally located between two un-crosslinked sections of tubing, said tubing assembly can be utilized to form a crosslinked balloon within the central crosslinked portion of the tubing assembly and thereafter, the balloon may be attached to the balance of the catheter shafts via the uncrosslinked outer ends of said balloon containing tubing assembly. FIG. 1A illustrates a non limiting embodiment of this method. Tube A consists of polymer materials that normally will not crosslink. Tubing B is consists of a material that normally will crosslink when exposed to crosslinking energy. Before applying crosslinking energy, tubing A is then preferably butt welded to both ends of tubing B to form a continuous tubing assembly containing a central crosslinkable section and outer non-crosslinkable sections. Upon exposure of the entire welded assembly to crosslinking energy, only the central portion of the assembly consisting of tubing B will crosslink while the ends of the assembly consisting of tubing A remain uncrosslinked. Thereafter the assembly can be utilized to form a crosslinked balloon from within the central crosslinked portion, while the uncrosslinked outer sections provide weldable ends. It should be noted that the polymer of tube B may require the addition of a functional material as described above in order to be crosslinkable upon exposure to crosslinking energy. In any event tubing A and B must be composed of compatible materials. For the purpose of this section, a compatible material means any material combinations that are weldable to each other.

Another embodiment for enabling a crosslinked or thermoset balloon to be welded to a thermoplastic catheter shaft would be to co-extrude or otherwise apply a layer of non crosslinkable polymer to the inner and/or outer surface of a crosslinkable polymer tube during or after the formation of the crosslinkable polymer tube and prior to (or possibly after) exposure of the tubing assembly to crosslinking energy. This would result in a tubing assembly with a non-crosslinkable layer on the inner and/or outer surface of a crosslinkable layer of tubing. When the tubing assembly is exposed to crosslinking energy, only the crosslinkable layer will crosslink, while the uncrosslinkable layer or layers will remain uncrosslinked. One can then utilize the resulting tubing to form a balloon in the manner previously described. Said balloon will comprise at least one layer which will be a crosslinked, and at least one surface which will be uncrosslinked and therefore weldable to the surface of another thermoplastic. FIG. 1B illustrates a non-limiting embodiment illustrating this method. A co-extruded tube assembly T, consisting of an inner layer A comprising a thermoplastic polymer material that normally will not crosslink and an outer layer B is comprising a material compatible with layer A, but which is crosslinkable when exposed to crosslinking energy. The entire co-extruded tubing comprising crosslinkable layer B and non crosslinkable layer A, is then exposed to crosslinking energy. Only the portion of the tubing consisting of outer layer B will crosslink while the inner portion of the tubing consisting of layer A will remain uncrosslinked. Since Layer A remains uncrosslinked and therefore a thermoplastic, it will be weldable to another thermoplastic. The tubing consisting of crosslinked outer layer B, and thermoplastic inner B could be utilized to form a balloon in the previously described manner. A balloon with a crosslinked outer layer B and a thermoplastic inner layer A would result. The ends C of the formed balloon could thereafter be placed over the catheter shafts D and E and welded thereto. In summary, if the uncrosslinked, thermoplastic and weldable layer comprises the inner lumen of the ends of the formed balloon element (as shown in FIG. 1B) then a weldable tube could be placed with the lumen of the ends of the balloon and welded thereto. Alternatively, if the uncrosslinked, thermoplastic and weldable layer comprises the outer layer of the ends of the formed balloon element (not shown), then ends of the balloon element could be placed within the lumen of another fuse weldable tube and welded thereto.

EXAMPLES

The following examples are intended to illustrate, but in no way limit the scope of the present invention.

Example 1

Preparation of Concentrate of Functional Material in Polymer

A concentrate consisting of 11% by weight of the co-agent Perkalink 301 (AKZO NOBEL) in 90% by weight Pebax 7233-SN01 (ATOCHEM) was prepared in a 35:125 mm Berstoff twin screw extruder, and pelletized. The Pebax was dried in a desiccant dryer to less than 0.04% and fed into the twin screw extruder using a loss in weight feeder under a dry nitrogen atmosphere. To minimize dwell time of the co-agent in the extruder, the co-agent was injected (in liquid form) at the next to last barrel section of the twin screw extruder using a screw designed for distributing liquids at low shear. The concentrate was evaluated for gels by extruding the prepared pellets in a ¾ inch Brabender 20:1 single screw with a 3:1 compression ratio screw through a 1" sheet die. The resulting film was evaluated visually and under magnification and no gels were visible at a melt temperature of 190 deg C. The concentrate was evaluated for uniform let down by dying a quantity of the concentrate pellets with a small amount of a transparent red dye. The dyed pellets were tumble mixed with native Pebax 7233-SN01 to yield about 1.5% by weight co-agent in the blend. The resulting blend was extruded in a ¾ inch Brabender 20:1 single screw with a 3:1 compression ratio screw through a 1" sheet die and evaluated for uniform color and lack of gels. The color was observed to be uniform and no gels were visible under magnification.

Example 2

Preparation of Crosslinked Tubing Using Functional Material Concentrate

Pebax 7233 SN01 tubing of dimension 0.033×0.019 inch containing 1.5% of the co-agent Perkalink 301 was prepared using the concentrate method described in Example 1. The tubing was extruded at a draw down ration of 2.7, and cut into 16 inch lengths. The tubing was packaged in polyethylene bags and irradiated using a 4.5 million volt RDI electron beam machine. Individual bags containing about 115 tubes per bags arranged in a single layer in the bags, were placed flat on carts and circulated multiple time through the electron beam path so as to accumulate a dose of 2.5 Mrad per pass. Tubing bags were collected at 2.5 Mrads, 5 Mrads, 7.5, and 12.5 Mrads. A portion of the un-irradiated tubing (0 Mrad) was set aside as a control. The tubing was evaluated for indications of being crosslinked by comparing the ultimate elongation of the un-irradiated tubing with the tubing irradiated at 2.5, 5, and 7.5 Mrads. The results presented in Table 1 show that the elongation decreased with increasing radiation dose. In addition the irradiated Pebax tubing no longer melted when tested with a hot soldering iron at about 300 deg C., while the un-irradiated tubing did melt when subjected to the same test. We concluded that the Pebax tubing containing co-agent crosslinked under the conditions specified above. It should be noted that Pebax tubing containing no co-agent, when exposed to e-beam radiation at 5 Mrads and tested with the hot soldering iron at about 300 deg C., melted. We conclude Pebax does not crosslink under the conditions specified in the absence of co-agent.

Example 3

Figure 2:
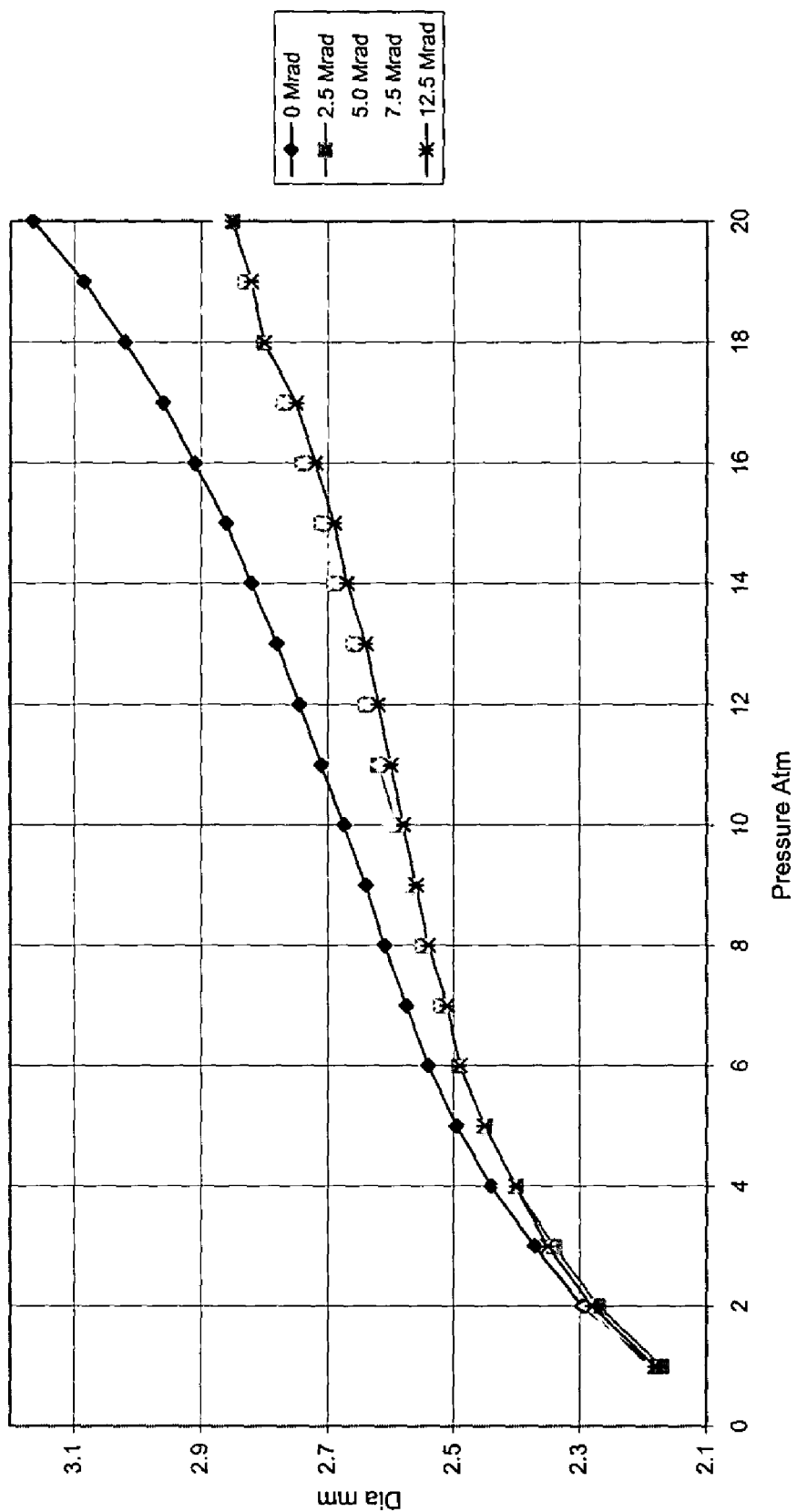
FIG. 2 is a chart of the compliance curves of a series of crosslinked and uncrosslinked 2.5 mm Pebax 7233 balloons.

Blowing of Balloons, and Compliance Curves Thereof Using Tubing Crosslinked at Different Levels Using the tubing prepared in Example 2, balloons 2.5 mm diameter and 20 mm length were blown using an Interface Associates (Laguna Niguel, Calif.) Model 9506H balloon forming machine. Balloons were blown at 210 deg F. and heat set at 260 deg F. The hoop ratio was 5.13. The balloons were deflated and removed from the mold and the double wall thickness was measured. The compliance curves of the un-irradiated balloons and the irradiated balloons at 0, 2.5, 5, 7.5 and 12.5 Mrads were evaluated using an Interface Associates model GPL-500 gas pressure leak tester with a compliance test fixture immersed in a 37 deg C. water bath. The balloon diameter at intervals of one (1) atmosphere were recorded and graphically plotted. The burst pressure was also recorded. The compliance curve results are presented in FIG. 2. It should be noted that the irradiated compliance curves are flatter than the un-irradiated compliance curve, and also there is less expansion at high pressures for the irradiated curves relative to the un-irradiated compliance curve.

Example 4

Effect of Various Heat Shrinking Conditions on 2.5 Mrad Crosslinked Balloons

Using the 2.5 Mrad tubing prepared in Example 2, balloons 2.5 mm diameter and 20 mm length were blown using an Interface Associates Model 9506H balloon forming machine. Balloons were blown at 210 deg F. and heat set at 260 deg F. The hoop ratio was 5.13. The balloons were deflated and removed from the mold. The double wall thickness of the blown balloon was recorded. The balloons were placed in a shrink fixture consisting of clamps and a circular heater approximately 3.5×20 mm ID. The unexpanded tubing ends of the deflated balloon were clamped so that no portion of the deflated balloon contacted the heater walls. At least one clamp was configured to allow the lumen within the clamp to remain open. The circular heaters were ramped from ambient to a specified designated shrink temperature in order to cause the deflated balloon to shrink radially while the clamps were held motionless to prevent axial shrinkage. The specified designated shrink temperature ranged from 180 deg F. to 300 deg F. in 20 deg increments. As soon as the designated shrink temperature was reached, the mold was cooled with chilled water. The balloon shrunk at a designated shrink temperature was thereafter removed from the shrink fixture, its double wall thickness recorded, and a compliance curve evaluated using an Interface Associates model GPL-500 gas pressure leak tester with a compliance test fixture immersed in a 37 deg C. water bath. The balloon diameter at intervals of one (1) atmosphere were recorded and graphically plotted. The burst pressure was also recorded. An family of compliance curves obtained at each shrink temperature is presented in FIG. 3.

Example 5

Effect of Various Heat Shrinking Conditions on 12.5 Mrad crosslinked Balloons

Using the 12.5 Mrad tubing prepared in Example 2, balloons 2.5 mm diameter and 20 mm length were blown using an Interface Associates Model 9506H balloon forming machine. Balloons were blown at 210 deg F. and heat set at 260 deg F. The hoop ratio was 5.13. The balloons were deflated and removed from the mold. The double wall thickness of the blown balloon was recorded. The balloons were placed in a shrink fixture consisting of clamps and a circular heater approximately 3.5×20 mm ID. The unexpanded tubing ends of the deflated balloon were clamped so that no portion of the deflated balloon contacted the heater walls. At least one clamp was configured to allow the lumen within the clamp to remain open. The circular heaters were ramped from ambient to a specified designated shrink temperature in order to cause the deflated balloon to shrink radially while the clamps were held motionless to prevent axial shrinkage. The specified designated shrink temperature ranged from 180 deg F. to 300 deg F. in 20 deg increments. As soon as the designated shrink temperature was reached, the mold was cooled with chilled water. The balloon shrunk at a designated shrink temperature was thereafter removed from the shrink fixture, its double wall thickness recorded, and a compliance curve evaluated using an Interface Associates model GPL-500 gas pressure leak tester with a compliance test fixture immersed in a 37 deg C. water bath. The balloon diameter at intervals of one (1) atmosphere were recorded and graphically plotted. The burst pressure was also recorded. An family of compliance curves obtained at each shrink temperature is presented in FIG. 4.

Figure 3:
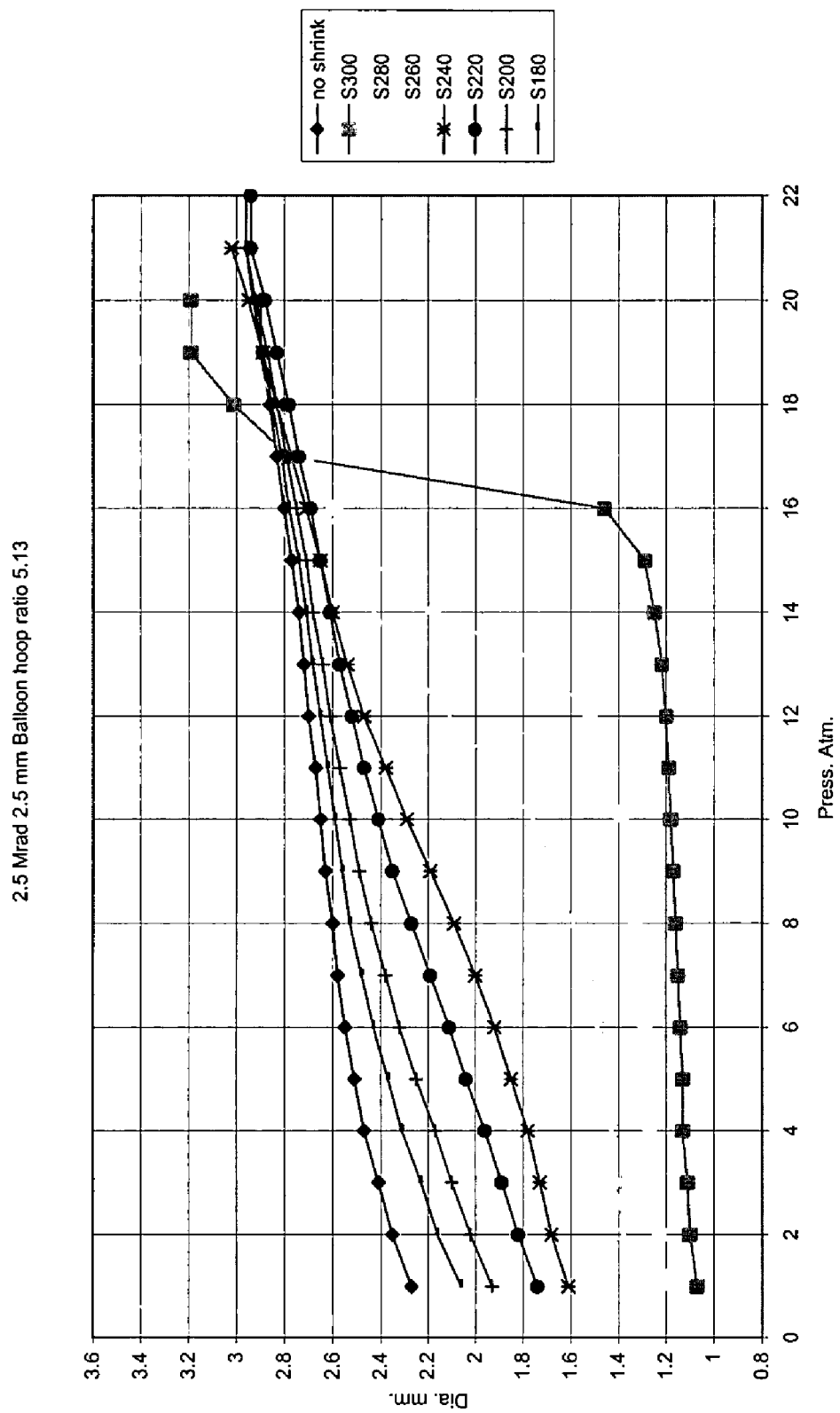
FIG. 3 is a chart of the compliance curves of a series of 2.5 mm Pebax 7233 balloons crosslinked at 2.5 Megarads and shrunk back at various temperatures.
Figure 4:
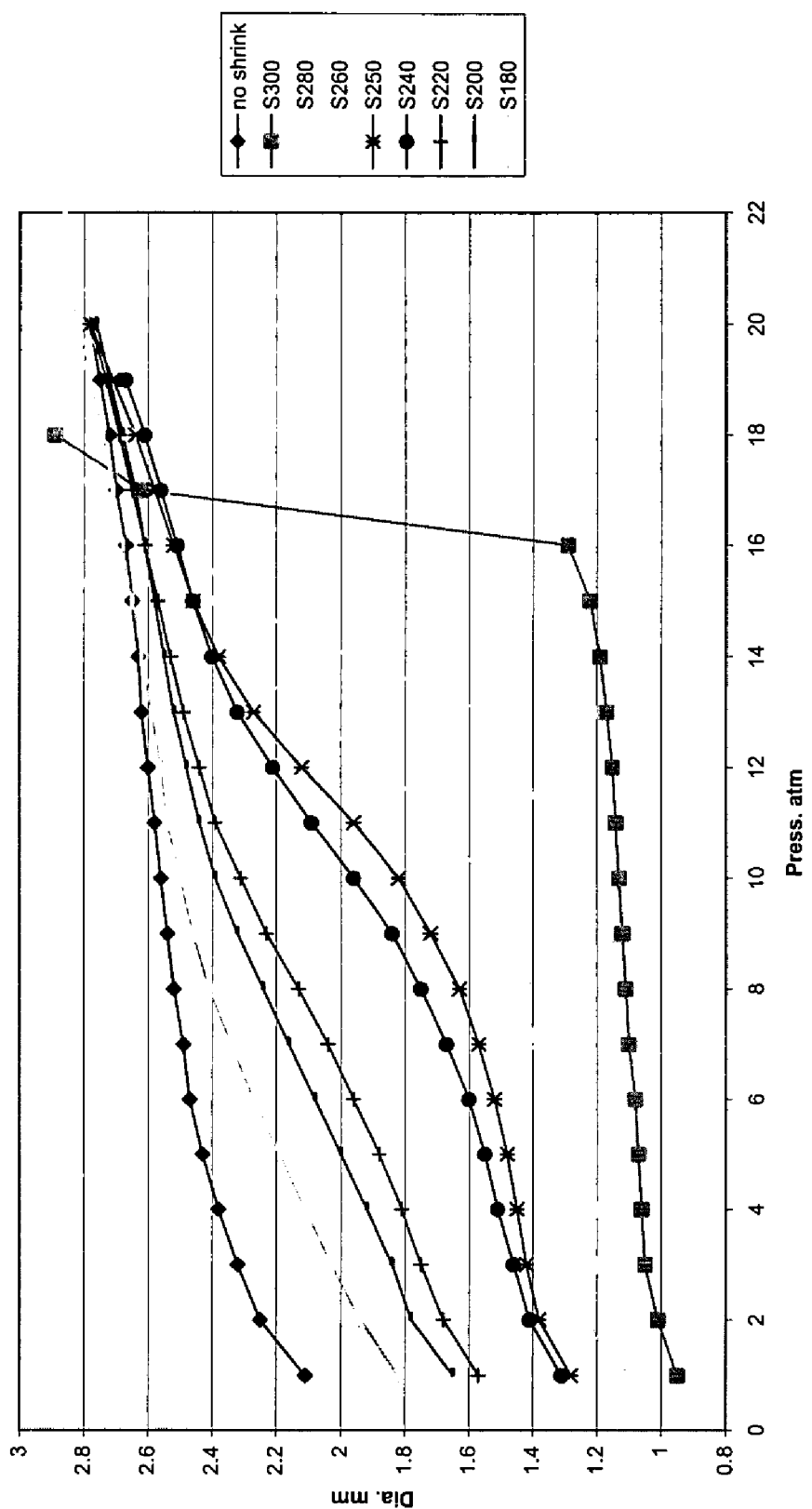
FIG. 4 is a chart of the compliance curves of a series of 2.5 mm Pebax 7233 balloons crosslinked at 12.5 Megarads and shrunk back at various temperatures.

Comparing FIG. 3 with FIG. 4 we note that the 12.5 Mrad balloons shrink to a smaller size for a given designated shrink temperature, than the 2.5 Mrad balloons. We also note that in the higher pressure regions, the compliance curves are relatively flat.

Example 6

Effect of Various Heat Shrinking Conditions on Un-Crosslinked Balloons

Using the 0 Mrad tubing (control) prepared in Example 2, balloons 2.5 mm diameter and 20 mm length were blown using an Interface Associates Model 9506H balloon forming machine. Balloons were blown at 210 deg F. and heat set at 260 deg F. The hoop ratio was 5.13. The balloons were deflated and removed from the mold. The double wall thickness of the blown balloons was recorded. The balloons were placed in a shrink fixture consisting of clamps and a circular heater approximately 3.5×20 mm ID. The unexpanded tubing ends of the deflated balloon were clamped so that no portion of the deflated balloon contacted the heater walls. At least one clamp was configured to allow the lumen within the clamp to remain open. The circular heaters were ramped from ambient to a specified designated shrink temperature in order to cause the deflated balloon to shrink radially while the clamps were held motionless to prevent axial shrinkage. The specified designated shrink temperature ranged from 180 deg F. to 300 deg F. in 20 deg increments. As soon as the designated shrink temperature was reached, the mold was cooled with chilled water. The balloon shrunk at a designated shrink temperature was thereafter removed from the shrink fixture, its double wall thickness recorded, and a compliance curve evaluated using an Interface Associates model GPL-500 or GPL-1000 gas pressure leak tester with a compliance test fixture immersed in a 37 deg C. water bath. The balloon diameter at intervals of one (1) atmosphere were recorded and graphically plotted. The burst pressure was also recorded. An family of compliance curves obtained at each shrink temperature is presented in FIG. 5.

Figure 5:
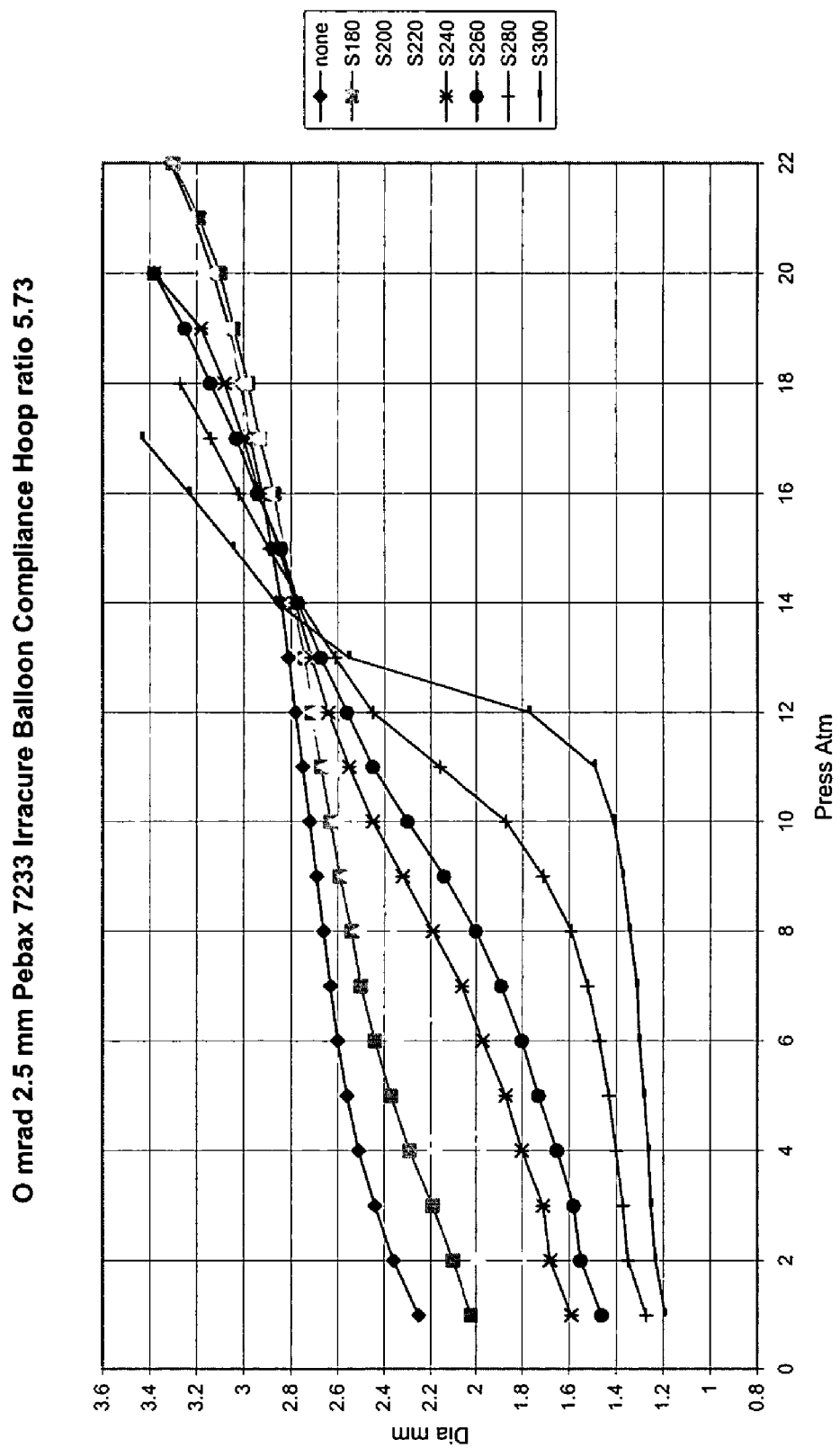
FIG. 5 is a chart of the compliance curves of a series of 2.5 mm Pebax 7233 balloons uncrosslinked and shrunk back at various temperatures.

Comparing FIGS. 3 and 4 with FIG. 5, we note that the 12.5 Mrad and 2.5 Mrad balloons shrink to a smaller size for a given designated shrink temperature, than the 0 Mrad balloons. We also note that in the higher pressure regions, the compliance curves for the 2.5 Mrad and 12.5 Mrad balloons are relatively flat, while the compliance curves for the 0 Mrad balloons curve upward in the region above 14 atmospheres.

Example 7

Co-Extruded Crosslinked Balloons for Weld Attaching to Catheter Shafts

Co-extruded Pebax 7233 SN01 tubing of dimensions 0.033 inch (OD)×0.019 inch (ID) consisting of a 0.005 inch thick outer layer containing 1.5% of the co-agent Perkalink 301 (prepared using the concentrate method described in Example 1) and an inner layer 0.001 inch thick of Pebax 7233 SN01 without any co-agent. The tubing was co-extruded at a draw down ration of 2.7, and cut into 16 inch lengths. The tubing was packaged in polyethylene bags and irradiated using a 4.5 million volt electron beam machine. Individual bags containing about 115 tubes per bags arranged in a single layer in the bags, were placed flat on carts and circulated multiple time through the electron beam path so as to accumulate a dose of 2.5 Mrad per pass. Tubing bags were collected at 2.5 Mrads, 5 Mrads, 7.5, and 12.5 Mrads. A portion of the un-irradiated tubing (0 Mrad) was set aside as a control. Using the co-extruded tubing, balloons 2.5 mm diameter and 20 mm length were blown using an Interface Associates (Laguna Niguel, Calif.) Model 9506H balloon forming machine. Balloons were blown at 210 deg F. and heat set at 260 deg F. The hoop ratio was 5.13. The balloons were deflated and removed from the mold. The balloons were trimmed so that a small length of slightly expanded tubing extended from each end of the balloon end cones. A small hot metallic rod was inserted into the lumen of the slightly expanded tubing extended from each end of the balloon end cones. It was observed for the irradiated samples that the inner lumen melted while the outer surface did not melt. This was confirmed for the irradiated samples by applying a hot metallic rod to the outer surface of the slightly expanded tubing extended from each end of the balloon end cones, and observing that the outer surface did not melt. For the un-irradiated co-extruded balloon samples, both the inner and outer surfaces melted upon application of a hot metallic rod.

A length of standard un-irradiated thermoplastic un-irradiated Pebax 7233 SN01 tubing was placed within the inner lumen of the slightly expanded tubing extending from an irradiated co-extruded balloon end cone and heat and pressure was applied using a TBW-318 tube welding machine (Interface Associates). The OD of the length of standard thermoplastic un-irradiated Pebax 7233 SN01 tubing was slightly smaller than the ID of the slightly expanded tubing extending from the balloon end cones. The two pieces were welded together in a pressure tight and smooth joint. When the same procedure was applied to a non co-extruded crosslinked balloon from Example 5, the two pieces did not weld together.

Example 8

Stent with Expansion Memory

Figure 1D:
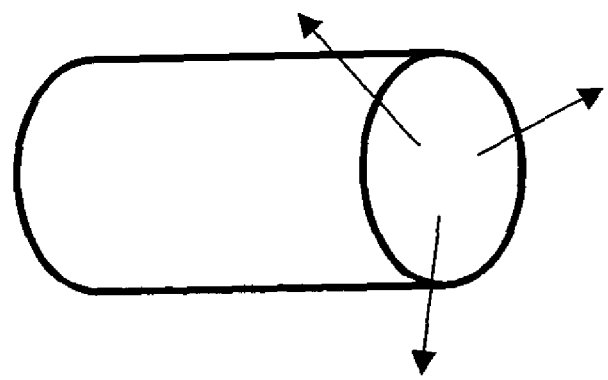
FIG. 1D is a drawing of a stent comprising a polymeric material with expansion memory.

A mandrel was placed within a crosslinked nylon 12 polymer tube of dimensions 0.117×0.107 inch (OD×ID). The OD of the mandrel was 0.035 inch. A length of teflon fluoropolymer 4:1 shrink tubing with an ID of 0.125 inch was slipped over the polymer tube, the ends of the tube were restrained (kept in fixed distance relative to each other), and heat was applied such that the nylon 12 softened and the shrink tubing compressed the nylon 12 around the mandrel. After stripping off the shrink tubing and removal of the mandrel, a reduced size smooth nylon 12 tubular member was obtained of approximate dimensions 0.035×0.065 inch. Upon immersion into warm water the reduced size tubular member expanded to approximately 0.117×0.107 inch (OD×ID). A typical expansion stent is depicted in FIG. 1D, in which the arrows indicate radial expansion. In such exemplary stent, longitudinal expansion is prevented.

Of course, it should be recognized that such expandable stents may be coupled to a catheter using numerous manners, including those described above (see e.g., FIGS. 1A and 1B). Consequently, it should be appreciated that a catheter may include a catheter balloon with expansion memory, in which the catheter has an outer diameter and wherein the catheter balloon has an outer diameter that is equal or less that the catheter outer diameter.

Thus, specific embodiments and applications of reduced profile medical balloon elements have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

TABLE 1

| DOSE (MRAD) | ELONGATION (%) |
| --- | --- |
| 0 | 551 |
| 2.5 | 528 |
| 5.0 | 494 |
| 7.5 | 457 |

PEBAX 7233; 019 × 033 Tubing

What is claimed is:

1. An axially restrained-shrunk catheter balloon comprising an axially stretched polymer wherein the catheter balloon is continuous and radially re-expandable.

2. The catheter balloon of claim 1 wherein the balloon is a compliant or semi-compliant catheter balloon.

3. The catheter balloon of claim 1 having a predetermined compliance curve that is attained at least in part by the axially restrained shrinkage of the balloon.

4. The catheter balloon of claim 3 wherein the predetermined compliance is a non-linear compliance curve.

5. The catheter balloon of claim 1 wherein the balloon is further coupled to a tubular element.

6. The catheter balloon of claim 5 wherein the balloon is welded to the tubular element.

7. The catheter balloon of claim 5 wherein the balloon has a balloon outer diameter and wherein the tubular element has a tubular element outer diameter, and wherein the balloon outer diameter and the tubular element outer diameter are the same.

8. The catheter balloon of claim 1 having a wall thickness that is less than a wall thickness of a polymer tube from which the catheter balloon is formed.

9. The shrunk catheter balloon of claim 1 having a non-linear compliance curve.

10. The shrunk catheter balloon of claim 1 comprising a crosslinked polymer or a polymer with shrink memory.

11. The shrunk catheter balloon of claim 1 wherein the shrunk catheter balloon is coupled to a wire-guided catheter.

12. A catheter comprising the catheter balloon of claim 1, wherein the catheter has an outer lumen diameter and wherein the catheter balloon has an outer diameter that is equal to or less than the catheter outer lumen diameter.

13. A catheter comprising the catheter balloon of claim 1, wherein the catheter has an outer lumen of a given diameter and wherein the catheter balloon has an outer diameter that is equal to or greater than the catheter outer lumen diameter.

14. A catheter comprising a catheter balloon according to claim 1, wherein the restrained-shrunk balloon has a reduced profile and the reduced profile is obtained without requiring the wrapping of the shrunk catheter balloon element about itself.

15. The catheter balloon of claim 1, having a reduced profile and comprising an expandable portion and a less expandable portion.

16. The catheter balloon of claim 15, wherein the expandable portion is between two less expandable portions.

17. The catheter balloon of claim 15, joined to a catheter to comprise a medical dilatation device.

18. The catheter balloon of claim 1, wherein an outer diameter of an expandable portion is a value between an outer diameter of a corresponding shrunken balloon and an outer diameter of the tube from which it is formed.

19. An axially restrained-shrunk catheter balloon comprising an axially stretched polymer wherein the catheter balloon is radially re-expandable and wherein the balloon comprises a crosslinked polymer.

20. The catheter balloon of claim 19 wherein the crosslinked polymer is crosslinked with a chemical crosslinker or wherein the crosslinked polymer is crosslinked using radiation.

21. The catheter balloon of claim 1 or 19 wherein the balloon comprises a stretch-oriented polymer.

22. A shrunk continuous catheter balloon produced by a process comprising:
   providing a polymer material formed into a tube;
   axially stretching the tube;
   forming a continuous balloon from the polymer material, and
   heating the balloon while restraining axial contraction in a controlled manner and thereby radially shrinking the axially stretched balloon.

23. A catheter comprising the shrunk catheter balloon of claim 22, wherein the catheter has an outer lumen diameter and wherein the shrunk catheter balloon has an outer diameter that is equal to or less than the catheter outer lumen diameter.

24. A catheter comprising the shrunk catheter balloon of claim 22, wherein the catheter has an outer lumen diameter and wherein the shrunk catheter balloon has an outer diameter that is equal to or greater than the catheter outer lumen diameter.

25. A catheter comprising a shrunk catheter balloon according to claim 22, wherein the shrunk catheter balloon has a reduced profile and the reduced profile is obtained without requiring the wrapping of the shrunk catheter balloon element about itself.

* * * * *